US006384198B1

(12) United States Patent
Diegel et al.

(10) Patent No.: US 6,384,198 B1
(45) Date of Patent: May 7, 2002

(54) METHODS FOR INHIBITING THE PRODUCTION OF HIV-1 RETROVIRUS USING MONOCLONAL ANTIBODIES AND FV SPECIFIC FOR CD2 ANTIGEN

(75) Inventors: Michael L Diegel, Kent; Peter S Linsley, Seattle; Lisa K Gilliland, Seattle; Patricia A Moran, Seattle; Joyce M Zarling, Seattle; Jeffrey A Ledbetter, Seattle, all of WA (US)

(73) Assignee: Bristol-Myers Sqibb Company, Princeton, NJ (US)

( * ) Notice: Subject to any disclaimer, the term of this patent is extended or adjusted under 35 U.S.C. 154(b) by 0 days.

(21) Appl. No.: 08/443,888

(22) Filed: May 31, 1995

Related U.S. Application Data

(62) Division of application No. 08/068,946, filed on May 25, 1993, now Pat. No. 5,795,572.

(51) Int. Cl.$^7$ ........................ C07K 16/28; C07K 16/46; A01N 1/02
(52) U.S. Cl. ...................... 530/390.1; 435/2; 530/387.1; 530/387.3; 530/388.1; 530/388.2; 530/388.22; 530/388.7; 530/388.73; 530/388.75
(58) Field of Search ........................... 530/387.3, 387.1, 530/388.2, 388.73; 388/22; 435/240.27, 172.2, 70.21, 454, 471; 424/85.8, 133.1, 135.1, 144.1, 130.1, 141.1, 112.1, 173.1

(56) References Cited

U.S. PATENT DOCUMENTS 5,629,162 A * 5/1997 de Fougerolles et al.
5,891,841 A * 4/1999 de Fougerolles et al.

FOREIGN PATENT DOCUMENTS

| WO | WO 88/09344 | 12/1988 |
| WO | WO 91/11194 | 8/1991 |
| WO | WO 93/06866 | 5/1993 |

OTHER PUBLICATIONS

W.B. Saunders Co Philadelphia 1981; p. 397 Dorland's Illustrated Medication Dictionary Twenty Sixth Edition.*
Merriam—Webster Inc, Springfield MA 1990; p. 366 Webster's Ninth New Collegiate Dictionary.*
Fahey et al. Clin Exp Immunol. 88:1–5 (1991).*
Daar et al. PNAS 87:6574–6578 (1990).*
Haynes et al. Annals of Medicine 28:39–41 (1996).*
Fox Biotechnology 12:128 (1994).*
Sommerfelt et al. J. Gen. Virol. 76: 1345–1352 (1995).*
Daar et al 1991 The American Journal of Medicine 90(Suppl 4A) pp. 4A–22S–4A–26S.*
Harris et al 1993 Tibtech 11:42–43.*
Schlesinger et al 1990 Cancer Detect. & Prev. 14(3):347–51.*
Bressler et al 1991 J. Immunol. 147:2290–2294.*
DeMaria et al 1991 J. Immunol. 146:2220–2226.*
Chester Kalter. Immunol. Lett 30:219–228 1991.*
G. Hale et al., "Remission Induction in Non–Hodgkin Lymphoma With Reshaped Human Monoclonal Antibody Campath–1H." *Lancet* 2:1394–1399 (Dec. 17, 1988).
D. Yasmeen et al., "The Structure and Function of Immunoglobulin Domains. IV. The Distribution of Some Effector Functions Among the $C\gamma_2$ and $C\gamma_3$ Homology Regions of Human Immunoglobulin G1," *J. Immunol.* 116:518–526 (1986).
K.B. Mullis & F.A. Faloona. "Specific Synthesis of DNA in Vitro Via a Polymer–Catalyzed Chain Reaction," *Meth. Enzymol.* 155:335–350 (1987).
K. Mullis et al., "Specific Enzymatic Amplification of DNA in Vitro: The Polymerase Chain Reaction." *Cold Spring Harbor Symp. Quant. Biol.* 51:263–273 (1986).
R.K. Saiki et al., "Primer–Directed Enzymatic Amplification of DNA with a Thermostable DNA Polymerase," *Science* 238:487–491 (1988).
E.Y. Loh et al., "Polymerase Chain Reaction with Single–Sided Specificity: Analysis of T–Cell Receptor $\delta$ Chain," *Science* 243:217–220 (1989).
Y.L. Chiang et al., "Direct cDNA Cloning of the Rearranged Immunoglobulin Variable Region," *Biotechniques* 7:360–366 (1989).
J.K. Batra et al., "Anti–TAc(Fv)–PE40 a Single Chain Antibody Pseudomonas Fusion Protein Directed at Interleukin–2 Receptor–Bearing Cells," *J. Biol. Chem.* 265:15198–15202 (1990).
P.S. Linsley et al., "Binding of the B Cell Activation Antigen B7 to CD28 Costimulates T Cell Proliferation and Interleukin 2 mRNA Accumulation," *J. Exp. Med.* 191:721–730 (1991).
A. Aruffo, "Transient Expression of Proteins Using COS Cells," in *Current Protocols in Molecular Biology* (2d ed., F.M. Ausubel et al., eds., John Wiley & Sons, New York, 1991) pp. 16.13.1–16.13.7.
P. Tijssen, "Practice and Theory of Enzyme Immunoassays" (Elsevier, Amsterdam, 1985), pp. 279–296.

(List continued on next page.)

*Primary Examiner*—Phillip Gambel
(74) *Attorney, Agent, or Firm*—Keith R. Lange; Christopher A. Klein

(57) ABSTRACT

An anti-CD2 monoclonal antibody according to the present invention can be: (1) a chimeric nonclonal antibody CD2 SFv-Ig produced by expression of the construct cloned in recombinant *Escherichia coli* culture ATCC No. 69277; (2) a monoclonal antibody having complementarity-determining regions identical with those of CD2 SFv-Ig; or (3) a monoclonal antibody competing with CD2 SFv-Ig for binding to CD2 antigen at least about 80% as effectively on a molar basis as CD2 SFv-Ig. Anti-CD2 monoclonal antibodies according to the present invention, as well as other antibodies that can modulate the interactions between T lymphocytes and monocytes, can be used to inhibit the production of HIV-1 by HIV-1-infected T cells in HIV-1-infected patients. In another use, T cells treated in vitro can be reinfused into AIDS patients to increase the proportion of functional non-HIV-1-producing T cells in the patient.

4 Claims, 4 Drawing Sheets

OTHER PUBLICATIONS

E. Harlow & D. Lane, "Antibodies: A Laboratory Manual" (Cold Spring Harbor Laboratory, Cold Spring Harbor, New York, 1988), pp. 324–339.

T.G. Wensel & C.F. Mears, "'Bifunctional' Chelating Agents for Binding Metal Ions to Proteins," in *Radioimmunoimaging and Radioimmunotherapy* (S.W. Burchiel & B.A. Rhodes, eds., Elsevier, Amsterdam, 1983), pp. 185–196.

A.R. Bradwell et al., "Developments in Antibody Imaging," in *Monoclonal Antibodies for Cancer Detection and Therapy* (Baldwin et al., eds., Academic Press, London, 1985) pp. 65–85.

J. DeMey et al., "Gold Probes in Light Microscopy," in *Immunocytochemistry: Modern Methods and Applications* (J.M. Polak & S. Van Noorden, eds., Wright, Bristol, 1986), pp. 71–88.

J. DeMey, "The Preparation and Use of Gold Probes," in *Immunocytochemistry: Modern Methods and Applications*, pp. 115–145.

W.O. Foye, ed., "Principles of Medicinal Chemistry" (3d ed., Lea & Febiger, Philadelphia, 1989), pp. 757–783.

E.S. Golub and D.R. Green, "Immunology: a Synthesis" (2d ed., Sinauer Associates, Inc., Sunderland, Mass., 1991), pp. 444–461.

P.J. Martin et al, "Identification and Functional Characterization of Two Distinct Epitopes on the Human T Cell Surface Protein Tp50," *J. Immunol.* 131:190–195 (1983).

M. Gilman, "Preparation of RNA from Eukaryotic and Prokaryotic Cells," in *Current Protocols in Molecular Biology* (2d ed., F.M. Ausubel et al., eds., John Wiley & Sons, New York, 1991), pp. 4.1.1–4.1.6.

H. Kaneoka et al., "Human T Lymphocyte Proliferation Induced by a Pan–T Monoclonal Antibody (Anti–Leu 4): Heterogeneity of Response is a Function of Menocytes," *J Immunol.* 131:158–164 (1983).

W.J.M. Tax et al., "Polymorphism in Mitogenic Effect of IgG1 Monoclonal Antibodies Against T3 Antigen on Human T Cells," *Nature* 304:445–447 (1983).

R.A.W. Van Lier et al., "Signals Involved in T Cell Activation. T Cell Proliferation Induced Through the Synergistic Action of Anti–CD28 and Anti–CD2 Moncolonal Antibodies," *Eur. J. Immunol.* 18:167–172 (1988).

C.D. Tsoukas et al., "Activation of Resting T Lymphocytes by Anti–CD3 (T3) Antibodies in the Absence of Monocytes," *J. Immunol.* 135:1719–1723 (1985).

H. Fischer et al., "Production of TNF–α and TNF–β by Staphylococcal Enterotoxin A Activated Human T Cells," *J. Immunol.* 144:4663–4669 (1990).

M.C. Psallidopoulos et al., "Integrated Proviral Human Immunodeficiency Virus Type 1 is Present in CD4$^+$Peripheral Blood Lymphocytes in Healthy Seropositive Individuals," *J. Virol.* 63:4626–4631 (1989).

E.J. Duh et al., "Tumor Necrosis Factor α Activates Human Immunodeficiency Virus Type 1 Through Induction of Nuclear Factor Binding to the NF–κB Sites In The Long Terminal Repeat," *Proc. Natl. Acad. Sci. USA* 86:5974–5978 (1989).

M.R. Smith & W.C. Greene, "The Same 50–kDa Cellular Protein Binds to the Negative Regulatory Elements of Interleukin 2 Receptor α–Chain Gene and the Human Immunodeficiency Virus Type 1 Long Terminal Repeat," *Proc. Natl. Acad. Sci. USA* 86:8526–8530 (1989).

J.E. Merrill et al., "Interleukin–I and Tumor Necrosis Factor α Can Be Induced From Mononuclear Phagocytes by Human Immunodeficiency Virus Type 1 Binding to the CD4 Receptor," *J. Virol.* 63:4404–4408 (1989).

L. Osborn et al., "Tumor Necrosis Factor α and Interleukin 1 Stimulate the Human Immunodeficiency Virus Enhancer by Activation of the Nuclear Factor κB," *Proc. Natl. Acad. Sci. USA* 86:2336–2340 (1989).

S.M. Schnittman et al., "Preferential Infection of CD4$^+$ Memory T Cells by Human Immunodeficiency Virus Type 1: Evidence for a Role in the Selective T–Cell Functional Defects Observed in Infected Individuals," *Proc. Natl. Acad. Sci. USA* 187:6058–6062 (1990).

L. Gazzolo & M.D. Dodon, "Direct Activation of Resting T Lymphocytes by Human T–Cell Lymphotrophic Virus Type I," *Nature* 326:714–717 (1987).

R.A. Gruters et al., "Selective Loss of T Cell Function in Differing Stages of HIV Infection," *Eur. J. Immunol.* 20:1039–1044 (1990).

S.M Schnittman et al., "The Reservoir for HIV–1 in Human Peripheral Blood is a T Cell That Maintains Expression of CD4," *Science* 245:305–308 (1989).

P. Dasgupta et al., "Myb Protein Binds to Human Immunodeficiency Virus 1 Long Terminal Repeat (LTR) Sequences and Transactivates LTR–Mediated Transcription," *Proc. Natl. Acad. Sci. USA* 87:8090–8094 (1990).

G. Nabel & D. Baltimore, "An Inducible Transcription Factor Activates Expression of Human Immunodeficiency Virus in T Cells," *Nature* 326:711–713 (1987).

S.E. Tong–Starksen et al., "Signalling Through T Lymphocyte Surface Proteins, TCR/CD3 and CD28, Activates the HIV–1 Long Terminal Repeat," *J. Immunol.* 142:702–707 (1989).

C.J.M. van Noesel et al., "Functional and Phenotypic Evidence for a Selective Loss of Memory T Cells in Asymptomatic Human Immunodeficiency Virus–Infected Men," *J. Clin. Invest.* 86:293–299 (1990).

U. Hazan et al., "Stimulation of a Human T–Cell Clone with Anti–CD3 or Tumor Necrosis Factor Induces NF–κB Translocation But Not Human Immunodeficiency Virus 1 Enhancer–Dependent Transcription," *Proc. Natl. Acad. Sci. USA* 87:7861–7865 (1990).

C.M. Walker & J.A. Levy, "A Diffusible Lymphokine Produced by CD8$^{+T\ Lymphocytes}$ Suppresses HIV Replication," *Immunology* 66:628–630 (1989).

P.A. Barry et al., "Cellular Factors Regulate Transactivation of Human Immunodeficiency Virus Type 1," *J. Virol.* 65:1392–1399 (1991).

Y. Lu et al., "The NFκB Independent cis–Acting Sequences in HIV–1 LTR Responsive to T–Cell Activation," *J. AIDS* 4:173–177 (1991).

L. Gilliland et al., "CD45 Ligation in T Cells Regulates Signal Through Both The Interleukin–2 Receptor and the CD–3/Ti T–Cell Receptor Complex," *Tissue Antigens* 35:128–135 (1990).

M.E. Sanders et al., "Human Naive and Memory T Cells: Reinterpretation of Helper–Inducer and Suppressor–Inducer Subsets," *Immunol. Today* 9:195–199 (1988).

H.E. Gendelman et al., "Restriction of HIV Replication in Infected T Cells and Monocytes by Interferon–α," *AIDS Res. Hum. Retroviruses* :1045–1049 (1990).

T.M. Folks et al., "Characterization of a Promonocyte Clone Chronically Infected With HIV and Inducible by 13–Phorbol–12–Myristate Acetate," *J. Immunol.* 140:1117–1122 (1988).

J.–M. Molina et al., "Induction of Tumor Necrosis Factor α and Interleukin 1β by Monocytic Cells Infected With Human Immunodeficiency Virus," *J. Clin. Invest.* 84:733–737 (1989).

J. B. Margolick et al., "Amplication of HTLV–III/LAV Infection by Antigen–Induced Activation of T Cells in Direct Suppression by Virus of Lymphocyte Blastogenic Responses," *J. Immunol.* 138:1719–1723 (1987).

G.P. Linette et al., "HIV–1–Infected T Cells Show a Selective Signaling Defect After Perturbation of CD3/Antigen Receptor," *Science* 241:573–576 (1988).

R.A. Gruters et al., "Non–Mitogenic T Cell Activation Signals Are Sufficient for Induction of Human Immunodeficiency Virus Transcription," *Eur. J. Immunol.* 21:167–171 (1991).

K.A. Clouse et al., "Monokine Regulation of Human Immunodeficiency Virus–1 Expression in a Chronically Infected Human T Cell Clone," *J. Immunol.* 142:431–438 (1989).

J.M. Zarling et al., "HIV–Infected Humans, but Not Chimpanzees, Have Circulating Cytotoxic T Lymphocytes That Lyse Uninfected CD4+Cells," *J. Immunol.* 144:2992–2998 (1990).

F. Plata et al., "AIDS Virus–Specific Cytotoxic T Lymphocytes in Lung Disorders," *Nature* 3287:348–351 (1987).

B.D. Walker et al., "HIV–Specific Cytotoxic T Lymphocytes in Seropositive Individuals," *Nature* 328:345–348 (1987).

J.E. Brinchmann et al., "CD8+T Cells Inhibit HIV Replication in Naturally Infected CD4+ T Cells. Evidence for a Soluble Inhibitor," *J. Immunol.* 144:2961–2966 (1990).

E.S. Daar et al., "Transient High Levels of Viremia in Patients With Primary Human Immunodeficiency Virus Type 1 Infection," *New Eng. J. Med.* 321:961–964 (1991).

D.D. Ho et al., "Quantitation of Human Immunodeficiency Virus Type 1 in the Blood of Infected Persons," *New Eng. J. Med.* 321:1621–1625 (1989).

R.W. Coombs et al., "Plasma Viremia In Human Immunodeficiency Virus Infection," *New Eng. J. Med.* 321–1626–1631 (1989).

J.E. Brinchmann et al., "In Vitro Replication of HIV–1 in Naturally Infected CD4$^{30}$ T Cells Inhibited by rIFNα$_2$ and by a Soluble Factor Secreted by Activated CD8+ T Cells, But Not By rIFNβ, rIFNγ, or Recombinant Tumor Necrosis Factor–α," *J. AIDS* 4:480–488 (1991).

P.A. Welch et al., "Human IL–7: A Novel T Cell Growth Factor." *J. Immunol.* 143:3562–3467 (1989).

H. Hock et al., "Interleukin 7 Induces CD4+ T Cell–Dependent Tumor Rejection," *J. Exp. Med.* 174:1291–1298 (1991).

A.E. Namen et al., "Stimulation of B–Cell Progenitors by Cloned Murine Interleukin–7," *Nature* 333:571–576 (1988).

P.J. Morrissey et al., "Recombinant Interleukin 7, Pre–B Growth Factor, Has Costimulatory Acitivity on Purified Mature T Cells," *J. Exp. Med.* 169:707–716 (1989).

G.D. Chazen et al., "IL–7 Is a T Cell Growth Factor," *Proc. Natl. Acad. Sci. USA* 86:5923–5927 (1989).

T. Hara et al., "Human T Cell Activation. II. A New Activation Pathway Used by a Major T Cell Population Via a Disulfide–Bonded Dimer of a 44 Kilodalton Polypeptide (9.3 Antigen)," *J. Exp. Med.* 161:1513–1518 (1985).

J.A. Ledbetter et al., "Role of CD2 Cross–Linking in Cytoplasmic Calcium Responses and T Cell Activation," *Eur. J. Immunol.* 18:1601–1608 (1988).

A. Pierres et al., "Triggering CD28 Molecules Synergize with CD2 (T11.1 and T11.2)–Mediated T Cell Activation," *Eur. J. Immunol.* 18:685–690 (1988).

R.A. Van Lier et al., "Immobilized Anti–CD3 Monoclonal Antibodies Induce Accessory Cell–Independent Lymphokine Production, Proliferation and Helper Activation In Human T Lymphocytes," *Immunology* 68:45–50 (1989).

J.D. Kaufman et al., "Phorbol Ester Enhances Human Immunodeficiency Virus–Promoted Gene Expression and Acts on Repeated 10–Base–Pair Functional Enhancer Element," *Mol. Cell. Biol.* 7:3759–3766 (1987).

T.D. Geppert & P.E. Lipsky, "Accessory Cell Independent Proliferation of Human T4 Cells Stimulated by Immobilized Monoclonal Antibodies to CD3," *J. Immunol.* 138:1660–1666 (1987).

C.D. Tsoukas et al., "Activation of Resting T Lymphocytes by Anti–CD3 (T3) Antibodies in the Absence of Monocytes," *J. Immunol.* 135:1719–1723 (1985).

R. Schwab et al., "Requirements for T Cell Activation by OKT3 Monoclonal Antibody: Role of Modulation of T3 Molecules and Interleukin 1," *J. Immunol.* 135:1714–1718 (1985).

M.L. Misfeldt, "Minireview: Microbial 'Superantigens'," *Infect. & Immun.* 58:2409–2413 (1990).

B. Fleischer, "Mini–review: T Lymphocyte–Stimulating Microbial Toxins as 'Superantigens'," *Med. Microbiol. Immunol.* 180:53–58 (1991).

M. Dohlsten et al., "Two Subsets of Human CD4+ T Helper Cells Differing in Kinetics and Capacities to Produce Interleukin 2 and Interferon–γ Can Be Defined by the Leu–18 and UCHL1 Monoclonal Antibodies," *Eur. J. Immunol.* 18:1173–1178 (1988).

D.E. Staunton et al., "Functional Cloning of ICAM–2, a Cell Adhesion Ligand for LFA–1 Homologous to ICAM–1," *Nature* 339:61–64 (1989).

P. Nortamo et al., "The Expression of Human Intercellular Adhesion Molecule–2 is Refractory to Inflammatory Cytokines," *Eur. J. Immunol.* 21:2629–2632 (1991).

A.R. de Fougerolles & T.A. Springer, "Intercellular Adhesion Molecule 3, a Third Adhesion Counter–Receptor for Lymphocyte Function–Associated Molecule 1 on Resting Lymphocytes," *J. Exp. Med.* 715:185–190 (1992).

T.A. Springer, "Adhesion Receptors of the Immune System," *Nature* 346:425–434 (1990).

T.A. Springer et al., "The Lymphocyte Function–Associated LFA–1, CD2 and LFA–3 Molecules: Cell Adhesion Receptors of the Immune System," *Annu. Rev. Immunol.* 5:223–252 (1987).

Y Shimizu et al., "Role of Adhesion Molecules in T–Cell Recognition: Fundamental Similarities Between Four Integrins on Resting Human T Cells (LFA–1, VLA–4, VLA–5, VLA–6) in Expression, Binding, and Costimulation," *Immunol. Rev.* 114:109–143 (1990).

G.A. Van Seventer et al., "Remote T Cell Co–Stimulation Via LFA–1/ICAM–1 and CD2/LFA–3: Demonstration With Immobilized Ligand/mAb and Implication in Monocyte–Mediated Co–Stimulation," *Eur. J. Immunol.* 21:1711–1718 (1991).

G.A. Van Seventer et al., "The LFA-1 Ligand ICAM-1 Provides an Important Costimulatory Signal for T Cell Receptor–Mediated Activation of Resting T Cells," *J. Immunol.* 144:4579–4586 (1990).

R. Pardi et al., "Heterogenous Distribution and Transmembrane Signaling Properties of Lymphocyte Function–Associated Antigen (LFA-1) in Human Lymphocyte Subsets," *J. Immunol.* 143:3157–3166 (1989).

N. Damle et al., "Differential Costimulatory Effects on Adhesion Molecules B7, ICAM-1, LFA-3, and VCAM-1 on Resting and Antigen–Primed CD4$^+$ T Lymphocytes," *J. Immunol.* 7:1985–1992 (1992).

Y. Van Kooyk et al., "Enhancement of LFA-1–Mediated Cell Adhesion by Triggering Through CD2 or CD3 on T Lymphocytes," *Nature* 342:811–813 (1989).

G.A. Van Seventer et al., "Analysis of T Cell Stimulation by Superantigen Plus Major Histocompatibility Complex Class II Molecules or By CD3 Monoclonal Antibody: Costimulation by Purified Adhesion Ligands VCAM-1, ICAM-1, but Not ELAM-1," *J. Exp. Med.* 174:901–913 (1991).

S.B. Kanner et al., "CD2/LFA-3 Ligation Induces Phospholipase–Cγ1 Tyrosine Phosphorylation and Regulates CD3 Signaling," *J. Immunol.* 148:2023–2029 (1992).

M.F. Gruber et al., "Re–Evaluation of the Involvement of the Adhesion Molecules ICAM-1/LFA-1 in Syncytia Formation of HIV-1–Infected Subclones of a CEM T–Cell Leukemic Line," *AIDS Res. & Hum. Retro.* 7:45–53 (1991).

M. Busso et al., "HIV–Induced Syncytium Formation Requires the Formation of Conjugates Between Virus–Infected and Uninfected T–Cells in Vitro," *AIDS* 5:1425–1432 (1991).

J. Hildreth & R.J. Orentas, "Involvement of a Leukocyte Adhesion Receptor (LFA-1) in HIV–Induced Syncytium Formation," *Science* 244:1075–1079 (1989).

A. Valentin et al., "The Leukocyte Adhesion Glycoprotein CD18 Participates in HIV-1 Induced Syncytia Formation in Monocytoid and T–Cells," *J. Immunol.* 144:934–937 (1990).

C. Vermot–Desroches et al., "Functional Epitope Analysis of the Human CD11a/CD18 Molecule (LFA-1, Lymphocyte Function–Associated Antigen 1) Involved in HIV-1–Induced Syncytium Formation," *Scand. J. Immunol.* 34:461–470 (1991).

A.G. Dalgleish et al., "The CD4 (T4) Antigen is an Essential Component of the Receptor for the AIDS Retrovirus," *Nature* 312:763–68 (1984).

P.J. Maddon et al., "The T4 Gene Encodes the AIDS Virus Receptor and Is Expressed in the Immune System and The Brain," *Cell* 47:333–348 (1986).

D.C. Kalter et al., "Inhibition of Human Immunodeficiency Virus in Monocytes by Monoclonal Antibodies Against Leukocyte Adhesion Molecules," *Immunol. Let.* 30:219–223 (1991).

H. Schuitemaker et al., "Biolgical Phenotype of Human Immunodeficiency Virus Type 1 Clones at Different Stages of Infection: Progression of Disease Is Associated With a Shift From Monocytotropic to T–Cell–Tropic Virus Populations," *J. Virol.* 66:1254–1360 (1992).

T.A. Waldmann, "Monoclonal Antibodies in Diagnosis and Therapy," *Science*, 252:1657–1662 (1991).

V. Brankovan et al., "The Cell Surface Phenotype of a Naturally Occurring Human Suppressor T–Cell of Restricted Specificity: Definition by Monoclonal Antibodies," *J. Immunol.* 131:175–179 (1983).

M.L. Diegel et al., "Regulation of HIV Production by Blood Mononuclear Cells from HIV–Infected Donors: II. HIV-1 Production Depends on T Cell–Monocyte Interaction," *AIDS Res. Hum. Retrovir.* 9: 465–473 (1993). (Exhibit 103).

J.S. Bromberg et al., "Anti–CD2 Monoclonal Antibodies Alter Cell–Mediated Immunity in Vivo," *Transplantation* 51: 219–225 (1991).

E. Routledge et al., "A Humanized Monovalent CD3 Antibody Which Can Activate Homologous Complement," *Eur. J. Immunol.* 21: 2717–2725 (1991). (Exhibit 105).

A.J. McMichael, ed., "Leucocyte Typing III: White Cell Differentiation Antigens" (Oxford University Press, Oxford, 1987), pp. 113–160. (Exhibit 106).

J.L. Fahey & R. Schooley, "Status of Immune–Based Therapies in HIV Infection and AIDS," *Clin. Exp. Immunol.* 88: 1–5 (1992). (Exhibit 107).

A. Wright et al., "Genetically Engineered Antibodies: Progress and Prospects," *Crit. Rev. Immunol.* 12: 125–168 (1992). (Exhibit 108).

P.A. Moran et al., "Regulation of HIV Production by Blood Mononuclear Cells from HIV–Infected Donors: I. Lack of Correlation Between HIV-1 Production and T Cell Activation," *AIDS Res. Hum. Retrovir.* 9: 455–464 (1993). (Exhibit 109).

* cited by examiner

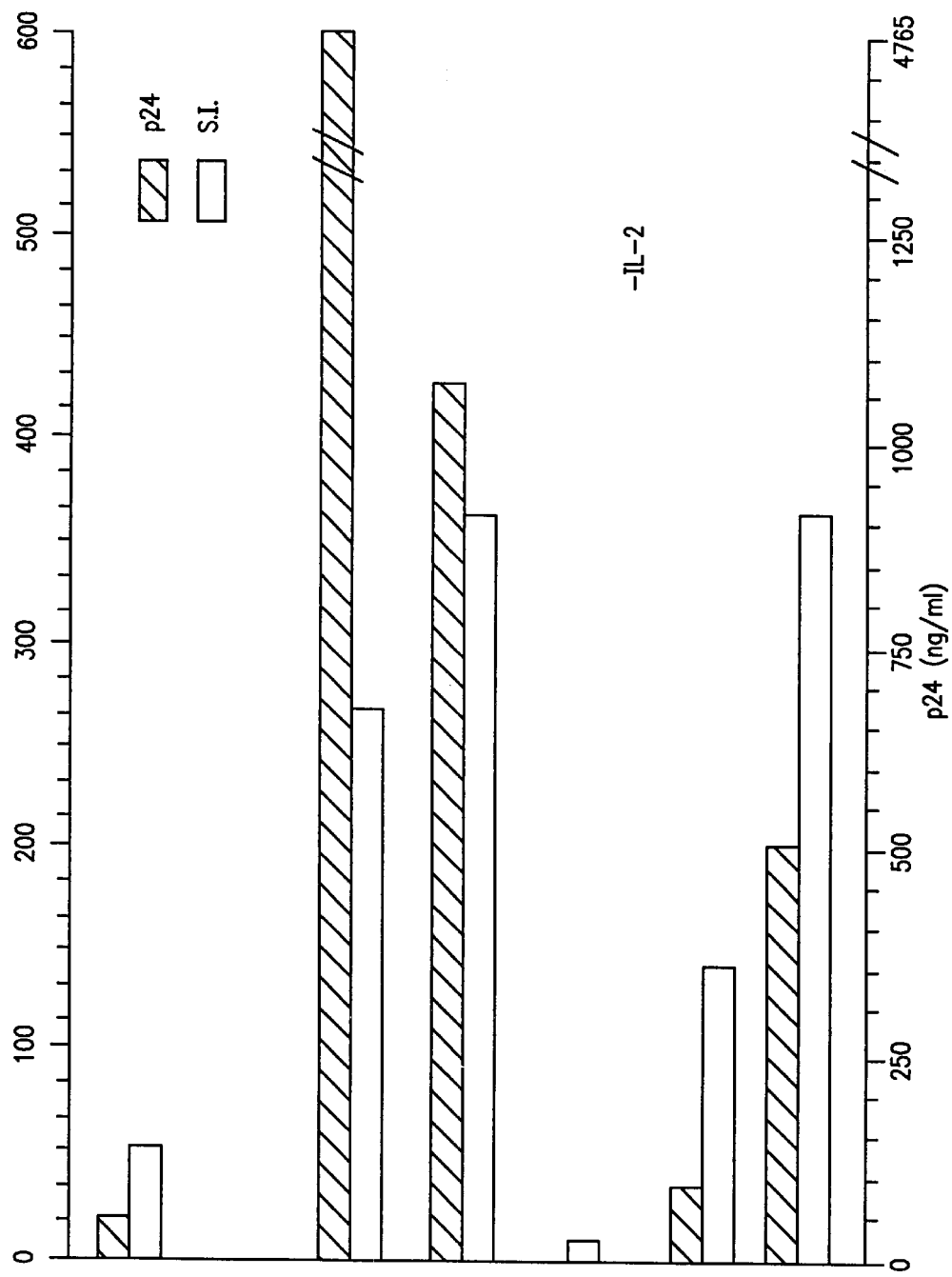
FIG. IB

METHODS FOR INHIBITING THE PRODUCTION OF HIV-1 RETROVIRUS USING MONOCLONAL ANTIBODIES AND FV SPECIFIC FOR CD2 ANTIGEN

This is a DIVISIONAL of application Ser. No. 08/068,946, filed May 25, 1993, now U.S. Pat. No. 5,795,572, issued on Aug. 18, 1998, which application(s) are incorporated herein by reference.

GOVERNMENT RIGHTS

This invention was made with government support under NIH grant RO1AI28065 to Joyce M. Zarling. The government has certain rights in the invention.

BACKGROUND OF THE INVENTION

This invention is directed to monoclonal antibodies and Fv specifically binding CD2 antigen and the use of such monoclonal antibodies in preventing the production of the human immunodeficiency virus (HIV-1) in HIV-1-infected T cells.

Acquired immunodeficiency syndrome (AIDS) has become one of the most feared diseases of the latter part of the twentieth century. In the United States alone, about 40,000 new cases of AIDS are diagnosed yearly and at least 200,000 cases have occurred since the disease became recognized about 1981. It is believed that from 1 million to 1.5 million Americans are infected with HIV-1, which means that they are at risk to develop AIDS and are likely to do so unless a means can be found for preventing the development of the full-blown illness in patients infected with the virus. Worldwide, the number of cases of AIDS runs into the millions, with certain areas of Africa and the Caribbean having the highest rates of infection.

Until now, although the amount of money spent for research on AIDS equals or exceeds that spent for research on diseases such as cancer and heart disease, no cure is yet available and the disease is considered uniformly fatal. Although several treatments have been developed that appear to slow the progression of the disease, at least in some patients, such as the drugs azidothymidine (AZT) and dideoxyinosine (DDI), these treatments are regarded only as palliatives. They do not work in all patients, and their effectiveness tends to decrease over the course of the disease. Thus, additionally treatments for AIDS are urgently needed.

It is generally believed that infection with the human immunodeficiency virus (HIC-1) is required for development of AIDS, although other factors may contribute to the establishment and the progress of the disease, because the disease is often associated with drug abuse and with exposure to other pathogens that may contribute to or enhance the immunosuppressive effects. HIV-1 is a retrovirus of the lentivirus subfamily. Like other retroviruses, its life cycle involves reverse transcription and incorporation of the viral RNA genome as DNA into the genome of the infected T cell. Activation of the virus results in transcription and translation, leading to production of the virus and depletion of $CD4^+$ T cells.

One of the characteristics of AIDS is the presence of opportunistic infections. These infections include diarrhea caused by several bacterial species, tuberculosis caused by avian and bovine mycobacteria, viral infections such as cytomegalovirus infection and shingles caused by herpesvirus, fungal infections such as candidiasis, aspergillosis, and histoplasmosis, and protozoan infections such as toxoplasmosis and pneumocystis pneumonia. These infections are frequently the actual cause of death in patients with AIDS, and case much morbidity even when not fatal. Although treatments exist for a number of these opportunistic infections, such as aerosolized pentamidine for pneumocystis pneumonia, these treatments are often unsuccessful because of the general health of the patients and their decreased resistance to infection brought about by AIDS itself.

Thus, improved methods of treating such infections are required.

Like other lentiviruses, HIV-1 can remain latent within the DNA of infected $CD4^+$ T lymphocytes, often for long periods. This latency is poorly understood, but is likely dependent on the state of activation of the host $CD4^+$ T cell (Z. F. Rosenberg & A. F. Fauci, "Minireview: Induction of Expression of HIV in Latently or Chronically Infected Cells," *AIDS Res. Hum. Retro,* 5: 1–4 (1989)).

Activation of T cells is dependent on a complex scheme of interactions between them and other cells designated as antigen presenting cells (ACs). These interactions are mediated by specific binding between molecules on the cell surface of T cells and molecules on the surfaces of APCs. One such interaction is between CS2 on the surface of T cells and its ligand LFA-3 on APC. The CD2 molecule, when crosslinked by anti-CD2 antibodies, is capable of directly activating T cells. The LFA-3 ligand is also referred to as a counter-receptor. Other receptor/counter-receptor pairs are ICAM-1/CD18 and CS28/B7.

One of the paradoxes that has complicated both the effort to understand AIDS and the effort to treat the opportunistic infections associated with it is that attempts by HIV-1-infected lymphocytes to respond to organisms responsible for opportunistic infections results in increased production of HIV-1 virus by infected cells. This is shown by results indicating that response to staphylococcal enterotoxin ("superantigen" or "SAg") increases HIV-1 production from infected cells in vitro.

Much remains to be understood about activation of HIV-1 production in infected lymphocytes. Various stimuli that have been shown to induce HIV-1 production by infected T-cell lines include the following: (1) T-cell antigens; (2) mitogens; (3) various cytokines such as TNFα, IL-1, and IL-6; and (4) other viruses (Rosenberg and Fauci (1989), supra; Z. F. Rosenberg & A. F. Fauci, "Activation of Latent HIV Infection," *J. NIH Res.* 2:41–45 (1990)).

However, relatively little is known about mechanisms that activate HIV-1 expression in $CD4^+$ T cells that contain integrated HIV-1 provirus.

Accordingly, there is a need for a method of suppression or blocking of HIV-1 production without markedly altering immunological functions and immune response to pathogens other than HIV-1, or, if some response is suppressed in order to prevent HIV-1 production, to do so without depressing the clinical status of the patient. Such a method would be useful in treating opportunistic infections and in extending the life of patients infected with HIV-1.

SUMMARY

We have developed a chimeric humanized single-chain recombinant antibody, CD2 SFv-Ig, specifically binding to CD2 antigen, that can be used to suppress HIV-1 virus production in HIV-1-infected T cells, as well as other antibodies specifically binding CD2 antigen. We have also developed methods for suppressing virus production and treating subjects infected with HIV-1 using CD2 SFv-Ig or other antibodies specifically binding antigens involved in the intercellular interaction between T lymphocytes and monocytes.

Antibodies according to the present invention includes a single-chain recombinant antibody selected from the group consisting of:

(1) chimeric single-chain recombinant antibody CD2 SFv-Ig produced by expression of the construct cloned in recombinant *Escherichia coli* culture ATCC No. 69277;

(2) a antibody having complementarity-determining regions identical with those of CD2 SFv-Ig; and (3) a antibody competing with CD2 SFv-Ig for binding to CD2 antigen at least about 80% as effectively on a molar basis as CD2 SFv-Ig.

Preferably, the antibody completes at least about 90% as effectively on a molar basis as CD2 SFv-Ig for binding to CD2 antigen.

The complementarity-determining regions of either H chain origin or L chain origin can be identical in sequence to those of cD2 SFv-Ig.

Preferably, the antibody is chimeric single-chain recombinant antibody CD2 SFv-Ig.

Another aspect of the invention is an antibody modified from the antibody described above by deletion of at least a portion of the Ig-derived amino acid sequence therefrom. The entire Ig-derived amino acid sequence can be deleted. Such an antibody can be derived from CD2 SFv-Ig.

The antibody can be labeled with a detectable marker. The detectable marker can be selected from the group consisting of enzymes, paramagnetic materials, members of the avidin-biotin specific binding pair, fluorophores, chromophores, chemiluminophores, heavy metals, and radioisotopes.

Alternatively, the antibody can be conjugated to a therapeutic agent. The therapeutic agent can be selected from the group consisting of antinenoplastic agents, lymphokines, and toxins. Suitable lymphokines include interleukins, interferons, and tumor necrosis factors, in particular, interleukin-2. Suitable toxins include ricin, pseudomonas exotoxin, and diphtheria toxin.

Another aspect of the invention is a pharmaceutical composition comprising:

(1) a chimeric humanized single-chain recombinant anti-CD2 antibody according to the present invention in a quantity sufficient to inhibit production of HIV-1 virus in infected T cells in a patient infected with HIV-1; and (2) a pharmaceutically acceptable carrier.

Another aspect of the invention is a recombinant *Escherichia coli* cell stably transformed by a construct capable of expressing CD2 SFv-Ig chimeric humanized single-chain recombinant antibody in mammalian cells and deposited with the American Type Culture Commission as ATCC No. 69277.

Yet another aspect of the invention is a DNA construct capable of expressing CD2 SFv-Ig chimeric humanized single-chain recombinant antibody in mammalian cells and including murine complementarity-determining regions and human constant regions.

Yet another aspect of the invention is a method for inhibiting the production of HIV-1 in HIV-1-infected T cells. The method comprises the steps of:

(1) selecting T cells infected with HIV; and (2) contacting the infected T cells with a antibody capable of disrupting cell-surface interactions between $CD4^+$ T lymphocytes and monocytes in order to inhibit the production of HIV-1 in the infected T cells, the cells being contacted with the antibody in a quantity sufficient to inhibit the production of HIV-1 in the contacted T cells.

Preferably, the antibody is specific for CD2 and blocks the binding with CD2 antigen with its counter-receptor LFA-3. More preferably, the antibody is a antibody according to the present invention as described above; most preferably, the antibody is CD2 SFv-Ig. The antibody can also be a monclonal antibody to CD18, a monoclonal antibody to counter-receptor LFA-3, or a monoclonal antibody to counter-receptor ICAM-1. The antibody can be conjugated to a therapeutic agent.

Another aspect of the present invention is a method for treating a subject infected with HIV-1. The method comprises the steps of:

(1) isolating T cells infected with HIV-1 from the subject;

(2) contacting the infected T cells with a antibody capable of disrupting cell-surface interactions between $CD4^+$ T lymphocytes and monocytes n order to inhibit the production of HIV-1 in the infected T cells, the cells being contacted with a quantity of the antibody sufficient to inhibit the production of HIV-1 in the contacted T cells; and (3) reinfusing the contacted T cells into the patient to increase the proportion of functional, non-HIV-1-producing T cells in the subject thereby to treat the subject.

In some cases, an additional step of activating the T cells before reinfusion can be desirable.

The same antibodies are preferred for this procedure as for the procedure, described above, of inhibiting HIV-1 production in HIV-1-infected cells. The antibody can also be conjugated to a therapeutic agent. The method can further comprise the step of treating the subject with at least one agent specific for an opportunistic infection associated with AIDS. The agent can be aerosolized pentamidine, isoniazid, rifampin, or amphotericin B.

Reinfusing the contacted T cells into the patient can reduce the complications associated with HIV-1 infection.

Antibodies of the present invention can also be used for in vivo treatment of patients infected with HIV-1. An in vivo treatment procedure comprises administering to a patient whose T cells are infected with HIV-1 a antibody capable of disrupting cell-surface interactions between $CD4^+$ T lymphocytes and monocytes in order to inhibit the production of HIV-1 in the infected T cells, the antibody being administered to the patient in quantity sufficient to inhibit the production of HIV-1 in infected T cells in the patient. The antibody can be conjugated to a therapeutic agent. Treatment can further comprise the step of treating the patient with at least one agent specific for an opportunistic infection associated with AIDS. The antibody can be administered to the patient during viremia.

BRIEF DESCRIPTION OF THE DRAWINGS

These and other features, aspects, and advantages of the present invention will become better understood with reference to the following description, appended claims, and the accompanying drawings wherein:

FIG. 1b is a graph indicating the effect of treatment with the same monoclonal antibodies as used in FIG. 1a in the absence of added interleukin-2;

DEFINITIONS

Figure 1A:
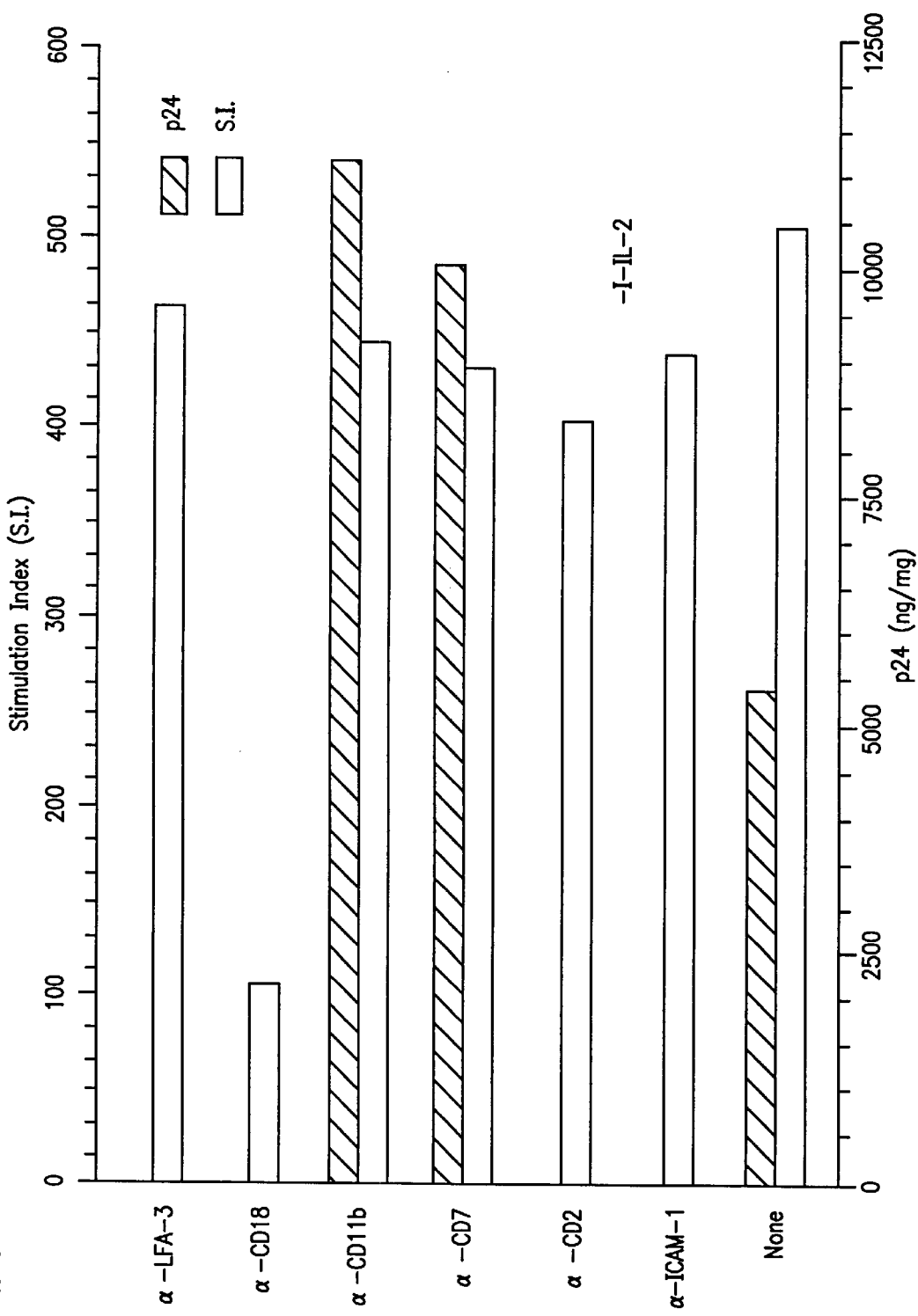
FIG. 1a is a graph indicating the effect of treatment with monoclonal antibodies to LFA-3, CD18, CD11b , CD7, Cd2, and ICAM-1 on production of the HIV-1 antigen p24 in HIV-1-infected lymphocytes in the presence of exogenous interleukin-2.

Definitions for a number of terms used in the following description, Examples, and appended claims are collected here for convenience.

"Monoclonal Antibody" means molecules having antibody activity and uniform in structure, binding affinity, and specificity, and includes chimeric monoclonal antibodies and monoclonal antibodies produced by recombinant DNA techniques in cells other than lymphocytes. "Monoclonal antibody" also includes bivalent or univalent antibody fragments, unless intact antibodies are specified.

"Identical", as applied to antibody molecules and amino acid sequences derived from antibody molecules or portions of antibody molecules, means identical in primary amino acid sequence. Two antibody molecules with the same primary amino acid sequence, but different patterns of glycosylation, are still identical by this definition.

"Specific Binding Affinity" means binding affinity determined by moncovalent interactions such as hydrophobic bonds, salt links, and hydrogen bonds on the surface of the binding molecules. Unless stated to the contrary, "specific binding affinity" implies an associated constant of at least about $10^6$ liters/mole for a bimolecular reaction.

"Human Origin" means identical to or recognizably derivable in structure or function from a sequence found in the human genome and doe snot require that the sequence be physically obtained from human cells, tissue, or body fluids. For example, a protein or peptide produced by translation of a gene or gene segment originally obtained from the human genome that is cloned into non-human mammalian cells, and which is isolated after expression in such non-human mammalian cells, is still of human origin. This remains true even if the protein or peptide occurs as a fusion protein associated with a protein from the non-human mammalian cells, as long as the translation product of the human sequence remains substantially intact relative to its original occurrence in human cells.

DESCRIPTION

We have discovered that certain monoclonal antibodies to cell-surface molecules involved in adhesions between T cells and other cells involved in the immune response, particularly monocytes, can inhibit production of HIV-1 virus by HIV-1-infected CD4+ T cells without inhibition of T-cell function or proliferation. Of the monoclonal antibodies suitable for inhibition of HIV-1 production, among the most useful is a novel, chimeric humanized anti-CD2 antibody produced in recombinant mammalian cells in culture and known as CD2 SFv-Ig. As described, this antibody contains murine variable regions and human constant regions within a single amino acid chain.

I. MONOCLONAL ANTIBODIES USEFUL FOR SUPPRESSION OF HIV-1 PRODUCTION

Among the monoclonal antibodies useful for inhibiting production of HIV-1 virus by infected lymphocytes are several monoclonal antibodies that disrupt interactions between T cells and monocytes. These antibodies are directed to cell surface molecules involved in cellular adhesion. Although applicants do not intend to be bound by this theory, it is believed that the processes of cellular adhesion are required in the cell-to-cell communication necessary for the establishment of the immune response, particularly for the development of specific immune activity by T cells presented with an antigen.

These antibodies include: (1) anti-CD2 monoclonal antibodies; (2) anti-CD18 monoclonal antibodies; (3) anti-LFA3 monclonal antibodies, and (4) anti-ICAM-1 antibodies. The CD2 and CD18 antigens are located on lymphocytes. The LFA-3 and ICAM-1 antigens are located on monocytes, with which T lymphocytes interact in the course of the immune response.

A. Anti-CD2 Monoclonal Antibodies

Among the most useful monoclonal antibodies for suppression of HIV-1 production by infected T-cells are anti-CD2 monoclonal antibodies. Anti-CD2 monoclonal antibodies were shown to inhibit HIV-1 production by about 80% to more than about 99%. Inhibition of HIV-1 production occurred in the presence or absence of exogenous interleukin-2 (IL-2). Importantly, CD4+ cell proliferation was maintained in the presence of exogenous IL-2, but HIV-1 production was markedly inhibited. Anti-CD2 monoclonal antibodies inhibited HIV-1 production by more than 90% at concentrations as low as 0.1 µg/ml of antibody. The addition of anti-CD2 monoclonal antibody is effective to suppress HIV-1 production even for T-cells activated by treatments with staphylococcal enterotoxin ("superantigen" or "SAG").

Among the useful anti-CD2 antibodies are monclonal antibodies designated 35.1, 9.6, and 9.1, although 9-1 binds a different epitope on CD2. However, of these monoclonal antibodies, 35.1 (*Leukocyte Typing III* (A. J. McMichael, ed., OxFord University Press, Oxford, 1987); *Leukocyte Typing IV* (W. Knapp et al., eds., Oxford University Press, Oxford, 1989)) is the most effective.

As shown below in Example 2, infra, the inhibitory effects of anti-CD2 monoclonal antibodies are not due to competition for human monocyte Fc receptors with activating α-CD3 monoclonal antibodies. This follows from the result that both F(ab'); and Fab fragments are effective to inhibit HIV-1 production. These fragments do not have the Fc portion of the antibody and therefore cannot compete for the monocyte Fc receptors. Accordingly, the use of such fragments is within the scope of the invention.

Another useful CD-2-specific monoclonal antibody for suppression of HIV-1 production in infected T-cells is a chimeric humanized anti-CD2 single-chain recombinant antibody produced by transient expression in COS cells and designated CD2 SFv-Ig. This singe-chain recombinant antibody contains a single peptide chain incorporating variable regions from both H and L chains of the murine monoclonal antibody 35.1, and constant regions from human IgGl. The vector used for transient expression of COS cells is amplified in *Escherichia coli,* deposited with the American Type Culture Collection 10801 University Boulevard, Man87725, Va. 20110-2209 as AT No. 69277, deposited on Apr. 9, 1993. This vector expresses CD2 SFv-Ig.

The protomeric form of this antibody is monovalent, i.e., each recombinant antibody molecule has only one antigen binding site. However, aggregates of this antibody can be produced. The production of this antibody is described in detail below.

Other antibodies having specific binding affinity for CD2 antigen and having at least some sequences of human origin are considered to be within the scope of the invention. These antibodies include: (1) a antibody having complementarity-determining regions identical with those of CD2 SFv-Ig and having at least one sequence segment of at least five amino acids of human origin; and (2) a monoclonal antibody competing with CD2 SPv-Ig for binding to CD2 antigen at least about 80% as effectively on a molar basis as CD2 SFv-Ig, and having at least one sequence segment of at least five amino acids of human origin. Preferably, the monoclonal antibody competes at least about 90% as effectively on a molar basis as CD2 SFv-Ig.

Antibodies having complementarity-determining regions substantially homologous with those of CD2 SPv-Ig can be generated from CD2 SFv-Ig by in vitro mutagenesis, using procedures known in the art and described, for example, in J. Sambrook et al., "Molecular Cloning: A Laboratory Manual" (2d et., Cold Spring Harbor Laboratory Press, Cold Spring Harbor, N.Y. 1989), vol. 2, ch. 15, "Site-Directed Mutagenesis of Cloned DNA," pp. 15.1–15.113, incorporated herein by this reference. Recombinant genetically engineered antibodies having complementarity-determining regions identical with those of CD2 SFv-Ig are derived from that chimeric antibody only by mutations in the constant regions or those portions of the variable regions that are not part of the complementarity-determining regions (CDRs). Recombinantly engineered antibodies with complementarity-determining regions substantially homologous to those of CD2 SFv-Ig can be derived from that antibody by mutations in both constant regions and variable regions, including CDRs.

Among the mutations that can be introduced into both constant and variable regions that substantially preserve affinity and specificity are mutations resulting in conservative amino acid substitutions. It is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments. Changes that do not affect the three-dimensional structure or the reactivity of the protein can be determined by computer modeling.

Among chimeric single-chain recombinant antibodies within the scope of the invention are those in which the complementarity-determining regions of H-chain origin are identical in sequence to those of CD2 SFv-Ig, and those in which CDRs of L-chain origin are identical in sequence to those of CD2 SFv-Ig.

Additional modifications of antibodies according to the present invention that are also within the scope of the invention include variants that eliminate at least part of the Ig region of the chimeric molecule, leaving the complementarity-determining regions of the antibody. These variants include variants that eliminate the entire Ig region of the molecule. These variants, which are smaller in molecular weight, can be more desirable for in vivo use, as they are more efficient in penetrating lymphoid tissues. These variants can be produced by in vitro mutagenesis, by inducing appropriate deletions. Preferably, these variants are derived from CD2 Srv-Ig and retain the complementarity-determining regions of that chimeric antibody.

Also within the scope of the invention for preventing replication of HIV-1 are anti-CS2 antibodies, in addition to 35.1, that block the LFA-3 binding site on CD2, thus preventing the interaction of CD2 with LFA-3.

B. Anti-CD18 Monoclonal Antibody

Another monoclonal antibody effective in suppressing HIV-1 production in CD4$^+$T cells is anti-CD18 monoclonal antibody. Antigen CD18 is the β subunit of a cell surface receptor known as LFA-1 and interacts with molecules designated ICAM-1, ICAM-2, and ICAM-3 on monocytes. Like monoclonal antibodies to CD2, monoclonal antibody to CD18 suppresses HIV-1 production in the presence or absence of exogenous IL-2, A suitable anti-CD18 monoclonal antibody is 60.3.

C. Anti-LFA-3 Monoclonal Antibody

Another antibody useful for suppressing HIV-1 production in infected T cells is an anti-LFA-3 monoclonal antibody. LFA-3 is a molecule typically found on the surface of monocytes and which interacts with CD2 on T-cell lymphocytes. Thus, anti-LFA-3 monoclonal antibodies disrupt interactions between CD2 and LFA-3 required for HIV-1 synthesis in activated lymphocytes. A suitable anti-LFA-3 monoclonal antibody is Ts2/9.

D. Anti-ICAM-1 Monoclonal Antibody

Yet another antibody useful for suppressing HIV-1 production in infected T-cells is an anti-ICAM-1 monoclonal antibody. (CAM-1, located on monocytes, binds the CD18 antigen on the surface of lymphocytes. CD18 is the β-subunit of LFA-1. A suitable anti-ICAM-1 monoclonal antibody is 84H10.

II. CHIMERIC HUMANIZED ANTI-CD2 ANTIBODIES

Among the preferred antibodies useful for suppressing HIV-1production and CD4$^+$ Lymphocytes is a chimeric humanized single-chain antibody designated CD2 SFv-Ig. The use of chimeric monoclonal antibodies is generally preferable in the treatment of human subjects because such monoclonal antibodies: (1) may induce less of a anti-murine immune response and (2) may have a longer survival time in vivo (G. Hale et al., "Remission Induction in Non-Hodgkin Lymphoma With Reshaped Human Monoclonal Antibody CAMPATH-1H, " *Lancet* 2:1394–1399 (1988); D. Yasmeen et al., "The Structure and Function of Immunogluobulin Domains. IV. The Distribution of Some Effector Functions among the C$\gamma_2$C$\gamma_5$ Homology Regions of Human Immunoglobulin Gl," *J. Immunol*, 116:518–526 (1986)).

A. Production of Chimeric Humanized Antibody CD2 SFv-Ig

The production of chimeric human antibody CD2 SFv-Ig requires the isolation of the genes coding for the monoclonal antibody in the murine hybridoma and the replacement of the constant regions by the corresponding gene sequences of the human constant regions. The final product is a single-chain molecule having the activity of monoclonal antibodies and expressed in COS cells after amplification of the DNA coding for the chimeric antibody in *Escherichia coli*.

1. cDNA Synthesis and Amplification

The first step in the production of CD2 SFv-Ig is the synthesis of cDNA from messenger RNA isolated from hybridoma cells producing anti-CD2 monoclonal antibody. Preferably, murine hybridoma cells are used.

Typically, total RNA is isolated by extraction methods well known in the art, such as extraction with phenol at acid pH or extraction with guanidinium thiocyanate followed by centrifugation in cesium chloride solutions. These procedures, and others for RNA extraction, are disclosed in J. Sambrook et al., "Molecular Cloning: A Laboratory Manual" (2ed., Cold Spring Harbor Laboratory Press, Cold Spring Harbor, N.Y., 1989), ch. 7, "Extraction, Purification, and Analysis of Messenger RNA From Eukaryotic Cells," pp. 7.1–7.25. Optionally, the mRNA can be isolated from the total mRNA by chromatography on oligo (dT) cellulose, but this step is not required.

To synthesize cDNA, primers complementary to the κ or λ light chain constant region and to the constant region of the $\gamma_{2a}$ heavy chain are preferably used to initiate synthesis. Most preferably, the primers used are complementary to nucleotides 101–124 in the κ chain constant region and to nucleotides 100–123 in the $\gamma_{2a}$ constant regions. Less preferably, other primers can be used, as long as they allow the production of cDNA incorporating the complete variable region.

Amplification can be carried out by any procedure allowing high fidelity amplification without slippage. Preferably, amplification is by the polymerase chain reaction procedure (K. B. Mullis & F. A. Faloona, "Specific Synthesis of DNA in Vitro Via a Polymerase-Catalyzed Chain Reaction," *Meth. Enzymol.* 155:335–350 (1987); K. Mullis et al., "Specific Enzymatic Amplification of DNA in Vitro: The Polymerase Chain Reaction," *Cold Spring Harbor Symp. Quant. Biol*, 51:263–273 (1986); R. K. Saiki et a., "Primer-Directed Enzymatic Amplification of DNA with a Thermostable DNA Polymerase," *Science* 238:487–491 (1988)).

One highly preferred procedure uses single-sided or anchored PCR (E. Y. Loh et al., "Polymerase Chain Reaction with Single-Sided Specificity: Analysis of T-cell Receptor & Chain," *Science* 243:217–220 (1989)). This procedure sues homopolymer tailing of the 3'-end of the reverse transcript; PCR amplification is then performed with a specific 3'-primer and a second oligonucleotide consisting of a homopolymer tail complementary to the homopolymer tail added to the 3'-end of the transcript attached to a sequence with a convenient restriction site, termed the anchor. In one version, degenerate oligonucleotides (Y. L. Chiang et al., "Direct cDNA Cloning of the Rearranged Immunoglobulin Variable Region," *Biotechniques* 7:360–366 (1989)) are used to amplify the $\gamma_{2a}$ heavy chain variable region by standard PCR, and after addition of a poly (dG) tail 3'-end to the cDNA for the ε chain variable region, anchored PCR is used using the primer complementary to nucleotides 101–124 of the constant region of the κ chain. Typically, about 30 rounds of amplification are performed, but this number can be varied if necessary.

2. Cloning of Amplified DNA

The PCR products are cloned into a suitable bacterial host, most preferably *E. coli,* with a plasmid vector into which the DNA can be incorporated and that can stably replicate in the bacterial host. A number of cloning vectors suitable for cloning into *E. coli* are known and are described in vol. 1 of Sambrook et al., supra, Ch.1, "Plasmid Vectors," pp. 1.1–1.110. The exact manipulations required depend on the particular cloning vector chosen and on the particular restriction endonuclease sites used for cloning into the vector.

One highly preferred vector is pUC19. For cloning into pUC19, the PCR products are treated with the Klenow fragment of *E. coli* DNA polymerase I and with the four deoxyribonucleoside triphosphates to obtain blunt ends by filling single-stranded regions at the end of the DNA chains. PCR can then be used to add Eco RI and Bam HI restriction sites to the 5'-end and 3'-ends, respectively, of the amplified fragment of cDNA of light-chain origin (the VL fragment). Similarly, Xba I and Hind III restriction sites are added to the amplified fragment of cDNA of heavy chain origin (the VH fragment). The fragments are digested with the appropriate restriction endonucleases and are cloned into pUC19 vector that had been digested with: (1) Eco RI and Bam HI for VL and (2) Xba I and Hind III for VH. The resulting constructs can be used to transform a competent *E. coli* strain such as DH5α.

Clones containing VL and VH are preferably identified by DNA sequencing. A suitable DNA sequencing procedure is the Sanger dideoxynucleotide chain termination procedure. Such a procedure can be performed using the Sequenase 2.0 kit (United States Biochemical, Cleveland, Ohio), with forward and reverse primers that anneal to the pUC19 sequence flanking the polycloning site. Preferably, consensus sequences for VL and VH are determined by comparing multiple clones and aligning the sequences with corresponding murine VL and VH variable region sequences (E. A. Kabat et al., "Sequences of Proteins of Immunological Interest" (4th ed., U.S. Department of Health and Human Services, Bethesda, Md. 1987).

3. Preparation of Expression Cassette and Generation of Single-Chain Antibody Construct The next step is the preparation of an expression cassette incorporating a single-chain antibody construct including the VL and VH sequences separated by a linker. In one highly preferred procedure, the 5'-leader sequence is removed from VL and replaced with a sequence containing a Sal I site preceding residue 1 of the native protein. The 33 constant region residues from the 3'-end are replaced with a primer adding a sequence complementary to a sequence coding for the 16-residue linker sequence ESGSVS-SEELAFRSLD (SEQ ID NO:1) (J. K. Batra et al., "Anti-TAc (FV)-PE40, a Single Chain Antibody Pseudomonas Fusion Protein Directed at Interleukin-2 Receptor-Bearing Cells," *J. Biol. Chem.,* 265:15198–15202 (1990)). For the VH sequence, a VH primer adds the "sense" sequence encoding the linker, e.g., the 16-residue linker sequence given above (SEQ ID NO:1) to the VH 5'-end preceding residue 1 of the mature protein and substitute a Bcl I site for the constant region residues at the 3'-end.

The polymerase chain reaction can then be used with a mixture of VL and VH cDNA, modified as indicated, as templates, and a mixture of the four primers (two linker primers and two primers containing restriction sites). This creates single DNA fragment containing a VL-linker-VH sequence flanked by Sal I and Bcl I sites. The DNA construct is then preferably passaged through dam *E. coli* cells, such as strain NEB 208. The passaged construct is then digested with Sal I and Bcl I.

4. Preparation and Expression of Fusion Protein

Digested DNA from the preceding step is then ligated into a pCDM8 vector containing the anti-L6 κ light chain leader sequence followed by a Sal I site and a Bcl I site preceding cDNA encoding a human IgGl tail in which cysteines in the hinge region are mutated to serines to inhibit dimerization (R. S. Linsley et al., "Binding of the B Cell Activation Antigen B7 to CD28 Costimulates T-Cell Proliferation and Interleukin-2 mRNA Accumulation," *J. Exp. Med.,* 191:721–730 (1991)).

The resulting construction is capable of expressing CD2 SFv-Ig chimeric humanized antibody in mammalian cells. This construct includes murine complementarity-determining regions and human constant regions. The construct is then preferably amplified in competent *E. coli*. A highly preferable strain of *E. coli* for transformation with the construct is MC1061/63. *E. coli* transformed with the construct has been deposited with the American Type Culture Collection as ATCC No. 69277.

Plasmid DNA is then isolated and purified, such as by cesium chloride density gradient centrifugation. The purified DNA is then transfected into a eukaryotic cell line capable of expressing such transfected DNA. A highly preferred cell line is monkey COS cells. A preferred method of introducing DNA is by DEAE-dextran, but other methods are available for transfection and are known in the art. These methods include transfection with coprecipitates of calcium phosphate and DNA, transfection using a polycation, Polybrene, and transfection by electroporation. These methods are described in J. Sambrook et al., "Molecular Cloning: A Laboratory Manual," supra, vol. 3, pp. 16.30–16.55.

Preferably, recombinant DNA containing the sequence coding for the fusion protein is expressed by transient expression, as described in A. Aruffo, "Transient Expression of Protein Using COS Cells," in *Current Protocols in Molecular Biology* (2d ed., F. M. Ausubel et al., eds., John Wiley & Sons, N.Y., 1991), pp. 16.13.1–16.13.7.

B. Structure and Properties of Chimeric Humanized Antibody, CD2 SFv-Ig

Chimeric humanized antibody to CD2 antigen, CD2 SFv-Ig, is a single chain structure containing portions of both H and L chain variable region of murine origin. The variable regions are linked to constant regions of human origin, namely IgG1. The resulting single chain protein binds CD2 antigen monovalently; i.e., there is one antigen binding site per IgG molecule. The antibody competes specifically with murine anti-CD2 monoclonal antibody 35.1 for binding to CD2 on Jurkat T Cells, as determined by fluorescent activated cell sorting (FACS).

III. LINKAGE OF ANTIBODIES TO DETECTABLE MARKERS AND THERAPEUTIC AGENTS

Antibodies according to the present invention, including CD2 SFv-IgG1, can be linked to detectable markers and therapeutic agents for use in diagnosis, both in vivo and in vitro, and for use in therapy. Among the detectable markers to which the antibodies can be linked are enzymes, paramagnetic ions or compounds, members of the avidin-biotin specific binding pair, fluorophores, chromophores, chemiluminophores, heavy metals, and radioisotopes. Among the therapeutic agents to which the antibodies can be linked are antineoplastic agents, lymphokines, and toxins.

Because the detectable markers and the therapeutic agents, as well as linkage methods, are well known in the art, the following discussion is intended to be exemplary rather than limiting. The emission of a particular detectable marker, therapeutic agent, or labeling method in the following discussion is not to be interpreted as implying that the detectable marker, therapeutic agent, or labeling method is unsuitable for use with any of the monoclonal antibodies of the present invention.

A. Linkage Methods

Suitable linkage methods include covalent linkage, linkage by chelation, and linkage by colloid formation.

1. Covalent Linkage

Covalent linkage includes both linkage by a bifunctional coupling agent and oxidative linkage. The former is generally applicable when the monoclonal antibody is linked to an organic molecule. The latter is most commonly used when the antibody is labeled with radioactive iodine.

a. Linkage by a Bifunctional Coupling Agent

Many bifunctional coupling agents are useful for coupling organic molecules possessing various types of functional groups to proteins, including antibody molecules. The conjugation of organic molecules to proteins, including proteins possessing antibody specificity, is well-known in the art and is described, for example, in P. Tijssen, "Practice and Theory of Enzyme Immunoassays" (Elsevier, Amsterdam, 1985). pp.. 279–296, incorporated herein by this reference.

Briefly, organic molecules containing carboxyl groups or that can be carboxylated, can be coupled by the mixed anhydride reaction, by reaction with a water-soluble carbodiimide, or esterification with N-hydroxysuccinimide. Carboxylation can be performed by reactions such as alkylation of oxygen or nitrogen substituents with haloesters, followed by hydrolysis of the ester, or the formation of hemisuccinate esters or carboxymethyloxines on hydroxyl or ketone groups of steroids.

Organic molecules with amino groups or nitro groups reducible to amino groups can be converted to diazonium salts and reacted with proteins at mildly alkaline pH, for aromatic amines. Organic molecules with aliphatic amines can be conjugated to proteins by various methods, including reaction with carbodiimides, reaction with the homobifunctional reagent tolyene-2,4-diisocyanate, or reaction with maleimide compounds. Aliphatic amines can also be converted to aromatic amines by reaction with p-nitrobenzoylchloride and subsequent reduction to a p-aminobenzoylamide, which can be then be coupled to proteins after diazotization. Also, bifunctional imidate esters, such as dimethylpimelimidate, dimethyladipimidate, or dimethylsuberimidate, can be used to conjugated amino group-containing organic molecules to proteins.

Thiol-containing organic molecules can be conjugated to proteins with malemides, such as 4-(N-maleimidomethyl)-cyclohexane-1-carboxylic acid N-hydroxysuccinimide ester.

For organic molecules with hydroxyl groups, an alcohol function can be converted to the hemisuccinate, which introduces a carboxyl group available for conjugation. Alternatively, the bifunctional reagent sebacoyldichloride converts an alcohol to an acid chloride, which then reacts with proteins.

Phenols can be activated with diazotized p-aminobenzoic acid, which introduces a carboxyl group, and can then be reacted with the proteins by the mixed anhydride reaction. Sugars can be activated by forming a p-nitrophenyl glycoside, followed by reduction of the nitro group to an amino group and conjugation by diazotization. Other methods include the cleavage of vicinal glycols of sugars to aldehydes by reaction with periodate, followed by coupling to amines by reductive alkylation with sodium borohydride. Alternatively, hydroxyl containing organic molecules can be conjugated after conversion to chlorocarbonates by reaction with phosgene.

For organic molecules with aldehyde or ketone groups, carboxyl groups can be introduced through the formation of O-carboxymethyloximes. Ketone groups can also be derivatized with p-hydrazinobenzoic acid to produce carboxyl groups. Organic molecules containing aldehydes can be directly conjugated through the formation of Schiff bases that are stabilized by reaction with a reducing agent such as sodium borohydride.

b. Oxidative Linkage

Oxidative linkage is particularly useful when coupling radioactive iodine to antibodies. Suitable methods include:

(1) chemical oxidation with clormaine-T; (2) chemical oxidation with iodogen (1,3,4,6-tetrachloro-3α,6α-diphenylglycoluril); (3) oxidation with the enzyme lactoperoxidase. Although not an oxidative procedure, another useful method for labeling with iodine is with [$^{125}$I] N-succinimidyl 3-(4-hydroxyphenylpropionate), generally known as Bolton-Hunter reagent. These techniques are described, e.g., in E. Harlow and D. Lane, "Antibodies: A Laboratory Manual" (Cold Spring Harbor Laboratory, Cold Spring Harbor, N.Y., 1988), pp. 324–339.

2. Linkage by Chelation

Linkage by chelation is particularly useful for positively-charged metal ions, which may be radioactive. An example of a suitable metal ion that can be linked to antibodies by chelation is $^{111}$In(III). Suitable chelating agents include derivatives of ethylenediaminetetraacetic acid (EDTA), such as the chelator diethylenetriaminepentaacetic acid (DPTA) and its derivatives. Procedures for labeling monoclonal antibodies by chelation are described, for example, in T. G. Wensel & C. F. Mears, "'Bifunctional' Chelating Agents for Binding Metal Ions to Proteins," in *Radioimmunoimaging and Radioimmunotherapy* (S. W. Burchiel & B. A. Rhodes, eds., Elsevier, Amsterdam, 1983), pp. 185–196 and A. R. Bradwell et al., "Developments in Antibody Imaging," in *Monoclonal Antibodies for Cancer Detection and Therpy* (Baldwin et al., eds., Academic Press, London, 1985), pp 65–85.

3. Linkage by Colloid Formation

Linkage of anitbodies to metal sols to form colloids is particularly useful to label antibodies for use in immunohistochemical or immunocytochemical techniques. The metal can be gold, plantium, silver, or other metals. This technique is described in detail, e.g., in J. DeMey et al., "Gold Probes in Light Microscopy," in *Immunocytochemistry: Modern Methods and Applications* (J. M. Polak & S. Van Noorden, eds., Wright, Bristol, 1986), pp. 71–88 and J. DeMey, "The Preparation and Use of Gold Probes," in *Immunocytochemistry: Modern Methods and Applications*, pp. 115–145.

B. Detectable Markers

1. Enzymes

Among useful detectable markers are enzymes that produce detectable products. In some cases, these products are insoluble and form colored precipitates that are readily detected. Among suitable enzymes are β-galactosidase, alkaline phosphatase, and horseradish peroxidase, as well as other enzymes known in the art.

2. Paramagnetic Materials

Paramagnetic materials include $Mn^{2+}$, $Cr^{3+}$, and many rare earths such as cerium, gadolinium, terbium, thulium, and their compounds.

3. Members of the Avidin-Biotin Specific Binding Pair

Antibodies can be labeled with a member of the avidin-specific binding pair and the other member of the specific binding pair can be labeled with another detectable marker. This provides an extremely specific means of indirect labeling of antibodies, and allows amplificaiton of the label. Preferably, the antibody is labeled with biotin and the indirect label is conjugated to avidin. In some cases, it may be desirable to reverse this pattern, labeling the antibody with biotin and attaching the label to avidin. Streptavidin, a protein from *Streptomyces avidinii*, has a similiar affinity for biotin and can be used as an alternative to avidin. Various linkers can be used to link biotin to antibodies, providing spacers of varying lengths.

4. Fluorophores

Frequently, fluorescent labels (fluorophores) are used to label antibodies for detection. Such flurophores include fluorescein, rhodamine, phycoerytrin, and Texas Red, a sulfonyl chloride derivative. Other fluorophores, including derivatives of these, can also be used to label antibodies.

5. Chromophores

A large number of dyes or chromophores can be used as labels to give a visual indication of antibody concentration, although other methods are generally more sensitive and can detect lower concentrations of antibodies. Virtually any dye can be coupled to antibodies, using one of the coupling procedure disclosed above.

6. Chemiluminophores

An alternative fluorophores is chemiluminophores (chemiluminescent labels). These labels include luminol and isoluminol derivatives, aryl oxalates, 10-methyl-acridinium-9-carboxylic acid aryl esters, and 5-methyl-phenanthridinium-6-carboxylic acid aryl esters, among others.

7. Heavy Metals

These include electron-dense metals such as gold, silver, or platinum. These are typically linked to antibodies by colloid formation, and detected by their high electron density in electron microscopy. Colloidal heavy metal labels can also be detected by other properties of the colloids.

8. Radioistopes

Radioisotopes are frequently used labels that can be detected with extremely high sensitivity by scintillation counting for β-emitting isotopes or well counting using thallium-activated sodium iodide crystal detectors for γ-emitting isotopes. Radiosotopes suitable for labeling monoclonal antibodies included $^{3}$H, $^{14}$C, $^{35}$S, $^{32}$P, $^{125}$I, and $^{131}$I. Of these, probably the most commonly used radioactive label is the γ-emitter $^{125}$I, which is inexpensive and readily detectable at high efficiency.

C. Therapeutic Agents

Monoclonal antibodies according to the present invention can be conjugated with therapeutic agents and then used to direct the therapeutic agents to CD2-expressing lymphoctyes. This allows administration of higher concentrations of such agents without the necessity of administering high systemic doses of them. This can diminish the occurrence of side effects that are otherwise frequent with the use of such therapetic agents. The use of monoclonal antibodies according to the present invention conjugated to therapeutic agents is not necessarily limited to the treatment or palliation of AIDS, but may prove beneficial in other conditions affecting lymphoctye functions, including autoimmune disorders.

Among the therapeutic agents that can be conjugated to monoclonal anitbodies according to the present invention are antineoplastic agents, lymphokines, and toxins. Monoclonal antibodies according to the present invention that are conjugated to radio-isotopes, as described above, can also be used for therapy.

1. Antineoplastic Agents

A number of antineoplstic agents are known to those skilled in the art, and are described, for example, in W. O. Foye, ed., "Principles of Medicinal Chemistry" (3d ed., Lea & Febiger, Philadelphia, 1989), pp. 757–783, and incorporated herein by this reference. Exemplary antineoplastic agents include: (1) antimetabolites such as methotrexate, 6-mercaptopurine, 6-thioguanine, cytarabine, 5-fluorouracil, and dacarbazine; (2) alkylating agents such as triethylenethiophosphoramide ("thiotepa"), chlorambucil, mephalan, cyclophosphamide, carmustine, lomustine, busulfan, mitomycin C, and cis-dichlorodiammineplatinum; (3) DNA-intercalating agents such as doxorubicin, daunorubicin, mitoxantrone, and bisantrene; (4) drugs with antibiotic activity such as actinomycin D, bleomycin, and anthramycin; and (5) other compounds such as procarbazine, hydroxyurea, and asparaginase.

2. Lymphokines

Lymphokines suitable for attachment to monoclonal antibodies include interferons, interleukins, tumor necrosis factors, and transforming growth factor. Interleukins include IL-1$\alpha$, IL-1$\beta$, IL-2, IL-3, IL-4, IL-5, IL-6, IL-7, IL-8, IL-9, IL-10. Tumor necrosis factors include TNF$\alpha$ and TNF$\beta$. Interferons include $\alpha$-INF, which has at least 20 subtypes, $\beta$-INF and $\gamma$-INF. Transforming growth factor includes TGF$\beta$. The properties of these lymphokines are briefly summarized in E. S. Golub and D. R. Green, "Immunology: a Synthesis" (2d ed., Sinauer Associates, Inc. Sunderland, Mass., 1991), pp. 444–461, incorporated herein by this reference.

3. Toxins

Useful toxins for immunotherapy include ricin, derived from castor oil, pseudomonas exotoxin, and diphteria toxin. Other such toxins are also known in the art.

IV. PHARMACEUTICAL COMPOSITIONS

Another aspect of the present invention is pharmaceutical compositions suitable for use in reducing the proliferation of HIV-1 in infected patients.

In general, a pharmaceutical composition according to the present invention comprises:

(1) a chimeric humanized as single-chain recombinant anti-CD2 antibody according to the present invention in a quantity sufficient to inhibit production of HIV-1 virus in infected T cells in a patient infected with HIV-1; and (2) a pharmaceutically acceptable carrier.

The chimeric humanized single-chain recombinant anti-CD2 antibody is preferably CD2 SFv-Ig, although other antibodies according to the present invention can also be used in the pharmaceutical compostion.

Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity. The particular carrier used depends on the conentraiton of the agent capable of blocking the immune defense suppresive effect and the intended route of administration. Typically, a pharmaceutical composition according to the present invention is injected by one of a number of conventional routes, such as intravenous, intradermal, intraperitoneal, or intramuscular.

V. METHODS FOR INHIBITING THE PRODUCTION OF HIV-1 in HIV-1 INFECTED T-CELLS

Another aspect of the invention is a method for inhibiting the production of HIV-1 in HIV1-infected cells. In general, this method comprises:

(1) selecting T-cells infected with HIV-1; and (2) contacting the infected T cells with a monoclonal antibody capable of disrupting cell-surface interactions between CD4$^+$T lymphocytes and monocytes in order to inhibit the production of HIV-1 in the infected T cells, the cells being contacted with a quantity of the antibody sufficient to inhibit the production of HIV-1 in the contacted T cells.

The antibodies described above can be used to inhibit the production of HIV-1 in HIV-1-infected T cells. It is generally preferred to use a chimeric humanized single-chain recombinant single chain antibody according to the present invention, especially CD2 SFv-Ig. However, other monoclonal antibodies can also be used, such as divalent monoclonal antibody to CD2, monoclonal antibodies to CD18, monoclonal antibodies to counter-receptor LFA-3, and monoclonal antibodies to counter-receptor ICAM-1. One can also use the natural CD2 ligand LFA-3 in a soluble form, such as extracellular domain fusion protein, for this purpose.

For CD2 SFv-Ig, concentration as low as 0.1 $\mu$g/ml inhibit virus production by more than 50%. For dimeric murine monoclonal antibody 35.1, concentrations as low as 0.01 $\mu$g/ml inhibit by more than 50%; concentrations as low as 0.10 $\mu$g/ml inhibit by more than 90%.

The antibody used can be conjugated to a therapeutic agent if desired.

Despite the higher concentration of the antibody required, the use of the chimeric humanized antibody CD2 SFv-Ig is generally preferred to avoid the possiblity of undesirable immune reactions from murine antibodies. Such interactions can not only cause undesirable side effects, but also can interfere with the activity of the administered antibodies themselves. The higher concentraion of the antibodies need not be necessary in some circumtances, such as if a bivalent SFv is generated or if the amino acid sequences surrounding the binding regions are modified to increase binding efficiency. This modification can be performed by standard techniques of in viro mutagenesis.

VI. METHODS FOR TREATING SUBJECTS INFECTED WITH HIV-1

The above method forms the basis for methods of treating subjects infected with HIV-1. Subjects infected with HIV-1 can be treated with antibodies and compositions of the present inventions either ex vivo or in vivo.

In general, the method of ex vivo treatment comprises: (1) selecting T cells infected with HIV-1; (2) contacting the T cells with the antibody, as described above; and (3) reinfusing the contacted T cells into the patient to increase the proportion of functional, non-HIV-1-producing T cells in the subject, thereby to treat the subject. In some cases, it can be preferable to include an additinal step of activating the T cells in vitro before reinfusing them. This can expand the effective T-cell population without increasing the viral burden.

The dosage range used can be selected in accord with the minimum doses specified above for particular antibodies. The dose can be adjusted by the treating physician according to the clinical status and resopnse of the patient. This includes the T-cell count of the patient and the presence or absence of particular opportunisitic infections. This process can reduce the complications of HIV-1 infection, including the occurence of opportunistic infections and dementia caused by proliferation of AIDS in central nervous system tissue.

The method can be used in conjunction with administration of antibiotics or other specific therapeutic agents for treating opportunistic infections associated with AIDS. Examples of such therapeutic agents include aerosolized pentamidine for *Pneumocystis carinii* pneumonia, isoniazid and/or rifampin for mycobacterial infections, and amphotericin B for *candidiasis*.

In general, the method of in vivo treatment comprises administering to a patient whose T cells are infected with HIV-1 a antibody capable of disrupting cell-surface interactions between CD4$^+$T lymphocytes and monocytes in order to inhibit the production of HIV-1 in the infected T cells. The antibodies are those described above. The quanity of antibody administered is sufficient to increase the proportion of functional, non-HIV-producing T cells in the patient or to inhibit the production of HIV-1 infected T cells, in accordance with the dosage guidance given above. Administration of antibody in vivo can reduce the complications associated with HIV-1 infection and can be performed during viremia.

The antibody administered in vivo can be conjgated to a therapeturic agent if desired, as described above.

This therapeutic method can be combined with the administration of antibiotics or other specific therapeutic agents for treating opportunistic infections associated with AIDS, as described above.

EXAMPLES

The invention is illustrated by means of the following Examples. These Examples are for illustrative purposes only and are not to be construed as limiting the invention.

Example 1

Preparation of CD2 SFv-Ig Chimeric Humanized Anti-CD2 Recombinant Antibody

A chimeric single chain antibody containing human constant regions, CD2 SFv-Ig, was produced by recombinant DNA techniques as follows:

cNDA Synthesis and Amplification:

Hybridoma cells expressing mouse anti-human CD2 antibody 35.1 (P. J. Martin et al., "Functionally Distinct Epitopes of Human Tp50," *J. Immunol.* 131: 190–195 (1983)) were grwon in IMDM supplemented with 10% fetal calf serum (FCS) and $5 \times 10^7$ cells were lysed by standard protcol (M. Gilman, "Current Protocols in Molecular Biology" (John Wiley & Sons, New York, 1990), vol. I, pp. 4.1.2–4.1.6) to isolate total cellular RNA. First strand cDNA for 35.1 immunoglobulin kappa light chain variable region (VL) and 35.1 IgG2a heavy chain variable region (VH) was synthesized using avian myeloblastosis virus (AMV) reverse transcriptase (Life Sciences, St. Petersburg, Fla.) and specific primers that were complementary to nucletoides 101–124 in the murine kappa chain constant region (mck-1) and nucleotides 100–123 in the murine IgG2a constant region (mIgG2a).

A poly(dG) tail was added to the 3'-strand of 35.1 VL cDNA using terminal deoxynucleotidyl transferase (Stragagene, La Jolla, Calif.) and mck-1. The second strand was generated by the anchored polymerase chain reaction (E. Y. Loh et al., "Polymerase Chain Reaction with Single-Sided Specificity: Analysis of T Cell Receptor & Chain," *Science* 243: 217–220 (1989)) using mck-1 as the specific 3'-primer.

Degenerate oligonucleotides (Y. L. Chiang et al., "Direct cDNA Cloning of the Rearranged Immunoglobulin Variable Region," *Biotechniques* 7:360–366 (1989)) were used to amplify the 35.1 VH sequences by a standard polymerase chain reaction procedure using thermostable *Thermus aquaticus* (taq) DNA polymerase (R. K. Saiki et al., Primer-Directed Enzymatic Amplification of DNA with a Thermostable DNA Plymerase," *Science* 239: 487–491 (1988)). For anchored and standard PCR reactions, cDNA (0.1–1.0 $\mu$g) was mixed 1.25 mM of each dNTP, 10 mM Tris-HCl (pH 8.3), 50 mM KCl, 1.5 mM $MgCl_2$, 5' and 3' primers at 10–25 pmole each, and 2 U of Taq DNA polymerase (Stratagene, La Jolla, Calif.) in a total volume of 100 $\mu$l. Samples were subjected to thirty rounds of temperature cycling using a Perkin-Elmer Cetus thermal cycler (Norwalk, Conn.). The resulting amplified DNA was purified using Geneclean™ (Bio101, LaJolla, Calif.).

Cloning of Amplified cDNA:

The PCR products were treated with the Klenow fragment of *Escherichia coli* DNA polymerase I (H. Klenow & I. Henningsen, "Selective Elimination of the Exonuclease Activity of the Deoxyribonucleic Acid Polymerase from *Escherichia coli* by Limited Proteolysis," *Proc. Natl. Acad. Sci. USA* 65: 168 (1970)) and dNTP to obtain fragments with blunt ends. PCR was used to add Eco RI and Bam HI restriction sites to the 5' and 3' ends of the VL cDNA fragment. Similarly, Xba I and Hind III restriction sites were added to the VH cDNA. The resulting fragmemts were digested with appropriate enzymes and were cloned into Eco RI- and Bam HI-digested or Xba I- and Hind III-digested pUC19 vector. The constructs were used to transform competent *E. coli* (strain DH5$\alpha$).

Clones containing VL and VH were identified by DNA sequencing using the Sequences 2.0 kit (United States Biochemical, Cleveland, Ohio) and forward and reverse primers which anneal to pUC19 sequences flanking the polycloning site. Consensus sequences for 35.1 VL and VH were determined by comparing multiple clones and by alignment of the sequences with other murine VL and VH variable region sequences (E. A. Kabat et al., "Sequences of Proteins of Immunological Interest" (4th ed., U.S. Department of Health and Human Services, NIH, Bethesda, Md., 1987)).

Preparation of Expression Cassette:

New primers were designed that removed the 5' leader sequence from VL and added a Sal I site precediing residue 1 of the mature protein. The 33 constant region residues from the 3' end were replaced by PCR using a primer that added a sequence complementary to the sequence encoding the 16-residue linker sequence ESGSVSSEELAFRSLD (SEQ ID NO: 1) (J. K. Batra et al., "Anti-Tac(FV)-PE40, a Single Chain Antibody Pseduomonas Fusion Protein Directed at Interleukin 2 Receptor-Bearing Cells," *J. Biol. Chem.* 265: 15198–15202 (1990)).

Also, a VH primer was designed that added the "sense" sequence encoding the linker to the VH 5' end preceding residue 1 of the mature protein and substituted a Bcl I site for the constant region residues at the 3' end. Polymerase chain reaction was used with a mixture of VL and VH cDNA as the template and a mixture of the 4 primers (100 pmole each of the linker primers and 25 pmole each of the primers containing the restriction sites; other reagents as before), to create a single DNA fragment containing a VL-linker-VH sequence flanked by Sal I and Bcl I sites. The DNA was passaged through *E. coli* cells (strain NEB208), purified using Geneclean™ (Bio101, La Jolla, Calif.), and digested with Sal I and Bcl I.

Expression of CD2 SFv-Ig Fusion Protein and Protein Analysis:

The DNA encoding linked CD2 VL and VH was ligated into a pCDM8 vector containing the anti-L6 immunoglobulin light chain leader sequence followed by a SAI I site and a Bcl I site preceding cDNA encoding a human IgGl tail in which the cysteines in the hinge region were mutated to serines to inhibit dimerization (P. S. Linsley et al., "Binding of the B cell Activation Antigen B7 to CD28 Costimulates T Cell Proliferation and Interleukin 2 mRNA Accumulation," *J. Exp. Med.* 173:721–730 (1991) ("Linsley et al. (1991a)").

The construct was amplified in *E. coli* strain MC1061/P3 and plasmid DNA was purified on CsCl gradients. The DNA was checked by sequencing before transfection into COS cells with DEAE-dextran and then expressed in COS cells by transient transfection (A. Aruffo, "Transient Expression of Proteins Using COS Cells,"in *Current Protocols in Molecular Biology* (2d ed., F. M. Ausubel et al., eds., John Wiley & Sons, New York, 1991), p. 16.13.1–16.13.7). COS cells were cultured overnight in DMEM supplemented with 10% FCS and for 6 more days in serum-free DMEM. Serum-free supernatant was collected and purified on a column containing Protein A-Sepharose™. (Repligen, Cambridge, Mass.). The bound protein was eluted in citrate buffer and dialyzed into PBS. Protein concentration was determined using a protein assay kit (BioRad, Richmond, Calif.).

Example 2

Inhibition of HIV-1 Production in HIV-1-Infected CD4+ T Cells by Treatment with Monoclonal Antibodies In order to determine the effect of a number of monoclonal antibodies, including the chimeric humanized anti-CD2 antibody of Example 1 on HIV-1 production in HIV-1-infected CD4+ T cells, the generation of the p24 antigen of HIV-1 was measured in cells treated with various monoclonal antibodies.

Monoclonal Antibodies (mAbs):

Hybridoma OKT3 (anti-CD3) was obtained from the American Type Culture Collection, Rockville, Md. The culture supernatant, containing the antibody, was purified by protein A Sepharose™ chromatography. Purified antibodies to LFA-3 (Ts 2/9) and ICAM-1 (84H10) were obtained from Dr. Nitkin K. Damle of Bristol-Myers Squibb Pharmaceutical Research Institute, Seattle, Wash. Purified mAbs 9.3 (anti-CD28), 35.1 (anti-CD2), G10-1 (anti-CD8), 60.3 (anti-CD18), 10.2 (anti-CD5), G3-7 (anti-CD7), FC-1 (anti-CD16), 1F5 (anti-CD20), 60.1 (anti-CD11b), and BB1 (anti-B7) were previously described (A. J. McMichael (ed.), "Leucocyte Typing III" (Oxford University Press, Oxford, England, 1987); W. Knapp et al. (eds.) "Leucocyte Typing IV" (Oxford University Press, Oxford, England, 1989)). Affinity-purified CTLA-4 immunoglobulin (Ig) was produced by CHO cells that were transfected with the CTLA-4 Ig cDNA expression gene as previously described (P. S. Linsley et al., "CTLA-4 Is a Second Receptor for the B Cell Activation Antigen B7," *J. Exp. Med.* 174: 561–569 (1991) ("Linsley et al. (1991b)"). Purified human mouse chimeric mAb, cL6, was provided by Dr. Hellstrom, Bristol-Myers Squibb, Seattle, Wash. Blocking antibodies to CD2 (mAb 35.1 (purified)) and to the CD2 counter-receptor LFA-3 (mAb Ts 2/9 (as ascites)), were used at 10 μg/ml for purified antibody, or at a final ascites dilution of 1:250 in complete medium. Purified antibody to ICAM-1 (mAb 84H10); to the ICAM-1 counter-receptor LFA-1 (also known as CD18), (mAb 60.3); to the CD28 counter-receptor B7 (mAb BB1), and the control mAbs CD7, G3-7, and human CD6 were also used at 10 μg/ml. Ascites fluids containing the respective mAb (Ts 2/9 and KB61) were generated in pristane primed Balb/c mice and partially purfied by ammonium sulfate precipitation.

Blood Donors:

Heparinized blood was obtained with informed consent from HIV-I infected asymptomatic as well as uninfected individuals.

Cell Separations:

Peripheral blood mononuclear cells (PBMC) were isolated by Ficol™-Hypaque™ density gradient centrifugation. Except where noted, PBMC for all experiments were depleted of CD8+, B cells, and NK cells by treatment with anti-CD8 mAb G10.1, anti-CD20 mAb IF5 specific for B cells, and anti-CD16 mAb FC1 specific for NK cells for 30 minutes at 4° C., followed by complement (C', low toxicity baby rabbit C', Pel-Freez, Brown Deer, Wis.) for 45 minutes at 37° C. The cells were washed and resuspended in complete medium (RPMI 1640 medium (Gibco, Grand Island, N.Y.)) supplemented with 10% heat-inactivated pooled normal human serum from seronegative donors, 10 mM HEPES, 2 mM L-glutamine, 100 U/ml penicilin, and 100 μg/ml streptomycin) and resuspended at $1 \times 10^6$ cells/ml.

PBMC Stimulation of $CD4^{3o}$ Cells from HIV-1-Infected Patients:

In most experiments, except as noted, $1 \times 10^5$ cells in 0.1 ml were stimulated with soluble (1 μg/ml) anti-CD3 mAb, either OKT3 (ATCC) or G19-4 (H. Kaneoka et al., "Human T Lymphocyte Proliferation Induced by a Pan-T Monoclonal Antibody (Anti-Leu 4): Heterogeneity of Response in a Function of Monocytes," *J. Immunol.* 131:158–164 (1983); W. J. M. Tax et al., "Polymorphism in Mitogenic Effect of IgG1 Monoclonal Antibodies Against T3 Antigen on Human T Cells," *Nature* 304:445–447 (1983)) in round bottom 96-well tissue culture plates (Falcon, Lincoln Park, N.J.). Factors (blocking or control mAb at 10 μg/ml, CTLA-4 at 10 μg/ml, and +/− purified IL-2 (Pharmacia) at 30 U/ml) were added at the time of activation for a final volume of 0.25 ml, then incubated at 37° C. with 5% $CO_2$ for 7 or more days for collection of supernatants for assay of p24 HIV-1-specific protein with ELISA (Genetic Systems, Seattle Wash.).

For superantigen (SAg) experiments, staphylococcal enterotoxins (Toxin Technology, Sarasota, Fla.) were added as a cocktail with a 1.8 μg/ml final concentration of total antigen. PBMC were incubated as with anti-CD3 stimulations and supernatants were collected for p24 antigen capture assay after 7 days of culture.

Proliferation Assays:

Four days after activation, quadruplicate 100-μl cell aliquots from each well were transferred to 96-well round bottom plates and labeled with 1.0 μCi/well of tritiated thymidine ([$^3$H]TdR, New England Nuclear, Boston, Mass.), Followed by incubation at 37° C. with 5% $CO_2$. Cells were collectd 6–16 hours later using a cell harvester and counted by liquid scintillation. The stimulation indices, S.I., were calculated by dividing the mean [$^3$H]TdR incorporation of stimulated (untreated) cells by the mean [$^3$H] TdR incorporation of unstimulated cells. Wells from which cells had been taken for proliferative assays were refed with complete medium and reincubated at 37° C. and 5% $CO_2$, for eventual measurement of p24 antigen as described below.

p24 Antigen Capture and ELISA Assay:

On day 7, except where noted, supernatants from quadruplicate wells were removed form PBMC cultures and measured for p24 antigen by ELISA (Genetic Systems, Seattle, Wash.). A standard curve was generated for each assay from which p24 values of unknown supernatant values were calculated. Percentages of p24 inhibition were based on the mean total p24 of 4 to 8 replicate wells, induced following stimulation with anti-CD3 or SAg alone.

Results:

Stimulation of patients' PBMC with soluble anti-CD3 induced high levels of HIV-1 production (up to or more than 10 μg/ml p24). In contrast, stimulation with immobilized anti-CD3 induced very low levels (less than 10 ng/ml p24). The level of p24 in supernatants of activated PBMC is proportional to the level of HIV-1 present as determined by infectivity in PHA blasts, and thus is a useful indication of HIV-1 proliferation.

To investigate the role of cell-cell interaction molecules involved in production of HIV-1 following soluble anti-CD3 activation, we tested the effect of mAb to several cell surface adhesion molecules that are known to be important for adhesion (the binding of cell surface molecules found on monocytes to cell surface molecules found on T cells).

FIGS. 1a and 1b show that mAb to LFA-3 or its counter-receptor CD2, or mAb to CD18 (the β subunit for LFA-1) or its counter-receptor ICAM-1, markedly inhibited HIV-1 production by PBMC, suggesting that cooperative engagement of each of these receptor/counter-receptor pairs is required for monocyte/T cell interaction leading to HIV-1 production.

MAb to CD2, LFA-3, or ICAM-1 inhibited HIV-1 production from 80% to more than 99%. Inhibition of HIV-1 production by mAb to CD2, or LFA-3, or CD18, or ICAM-1 occurred in the presence or absence of exogenous IL-2. However, without exogenous IL-2, CD4+ T cell proliferation was markedly reduced in anti-CD3 activated cultures treated with mAb to CD2, or CD18, or LFA-3 (mAb to ICAM-1 inhibited proliferation to a lesser extent in some donor PBMC). Importantly, CD4+ T cell proliferation was maintained in the presence of exogenous IL-2 (FIG. 1a) yet HIV-1 production was markedly reduced. This is significant because $CD4^+$ T cell proliferation is important for developing resistance to the opportunistic infections that characterize AIDS.

Figure 2:
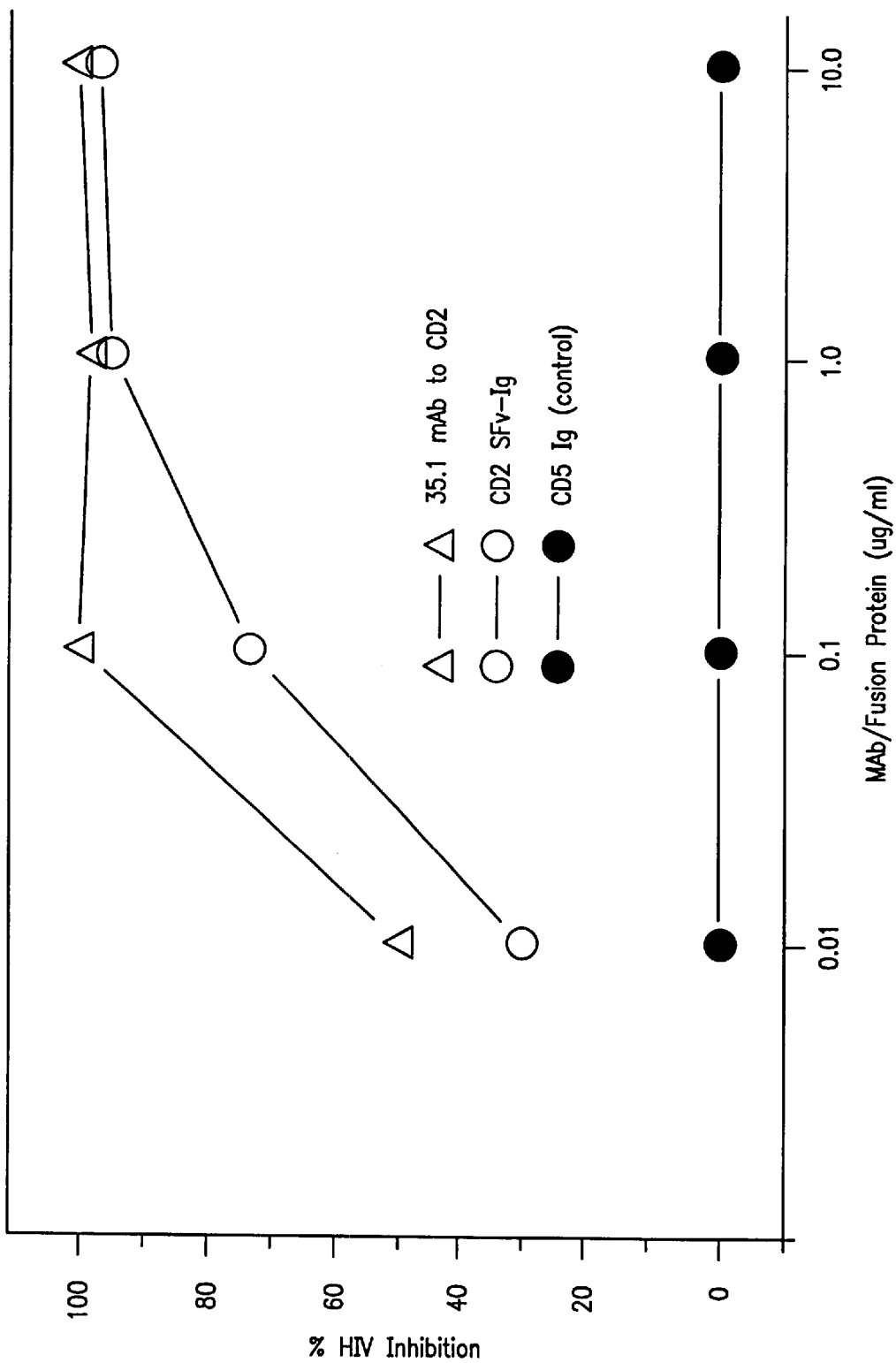
FIG. 2 is a graph showing a dose-response curve for treatment of infected cells with chimeric humanized single-chain recombinant antibody CD2 SFv-Ig, murine anti-CD2 monoclonal antibody, and CD5-Ig fusion protein antibody as a control, plotted against the inhibition of production of HIV-1 p24 antigen.

Anti-CD2 (mAb 35.1) inhibited HIV-1 production by more than 90% at concentration as low as 0.1 $\mu$g/ml of antibody (FIG. 2). The marked inhibition of p24 production observed with mAb 35.1 was consistently observed in six separate experiments, with PBMC from two donors per experiment. Addition of anti-CD2 up to, but not after, 24 hours post-stimulation with anti-CD3 was effective at inhibiting HIV-1 production.

These results suggest that interruption of CD2/LFA-3 interactions at early time points following activation are more important for inhibiting of HIV-1 production than blocking T cell-monocyte interactions at later time points (i.e., after 24 hours post-activation).

Blocking of CD2/LFA-3 interaction with mAb 35.1 to CD2 was shared by other CD2 mAbs, 9.6 and 9-1; however, 35.1 was most effective at inhibiting HIV-1 production, either reflecting epitope or affinity differences in CD2 mAbs. Inhibition of HIV-1 production by anti-LFA-3 was also reproducible in experiments in which PBMC from a number of seropostive donors were activited with anti-CD3.

CTLA-4 Ig, a CD28 homolog, also inhibits anti-CD3 induced HIV-1 production. CTLA-4 is analogous to CD28 on T cells in that both of these molecules bind B7 on monocytes (Linsley et al. (1991b), supra). Costimulation (i.e. augmentation of T cell receptor (TCR) signaling by cell surface molecules such as CD28, CD2, LFA-1 and others) of CD28 and TCR has been shown to induce high levels of IL-2 production (R. A. W. Van Lier et al., "Signals Involved in T Cell Activation: T Cell Proliferation Induced Through the Synergistic Action of Anti-CD28 and Anti-CD2 Monoclonal Antibodies," Eur. J. Immunol. 18:167–172 (1988)) and IL-2 mRNA accumulation (Linsley et al. (1991a), supra). To determine what effect blocking of the CD28/B7 pathway has on HIV-1 production, soluble recombinant CTLA-4 Ig fusion protein (Linsley et al. (1991b), supra)) or mAb to CD28 (9.3) or B7 (BB1) was added to anti-CD3 activated PBMC in the presence or absence of exogenous IL-2.

The results in Table 1 show that CTLA-4 Ig inhibited HIV-1 production by more than 70%. The mAbs BB1 and 9.3, anti-B7 and anti-CD28, respectively, did not inhibit HIV-1 production. CTLA-4 Ig binds to B7 with higher affinity than the mAb BB1 (Linsley et al. (1991b), supra, and is a more potent inhibitor of B7/CD28 engagement.

Anti-CD28 also had marginal effects on HIV-1 production because this mAb may substitute for B7/CD28 interaction and partially stimulate CD28 receptor on T cells. This is indicated by the much higher levels of T cell proliferation seen with anti-CD3 in the presence of anti-CD28, without exogenous IL-2 addition (Table 1). However, HIV-1 inhibition by CTLA-4 Ig was less than 40% when IL-2 was added to anti-CD3 activated PBMC. CTLA-4 Ig has been shown to inhibit endogenous IL-2 production. Therefore, CTLA-4 inhibition of HIV-1 production was partly related to decreased endogenous IL-2 production, resulting in decreased proliferation of CD4+ T cells and probably a decreased production and/or spread of HIV-1.

TABLE 1

EFFECT OF CTLA-4 Ig ON ANTI-CD3-INDUCED HIV-1 PRODUCTION

| Anti-CD3 stimulation of PBMC | Protein added | p24, ng/ml | % HIV Inhibition | S.I |
|---|---|---|---|---|
| +IL-2 | none | 716 | — | 232 |
| | CTLA-4 Ig | 454 | 36 | 270 |
| | α-cL6 | 796 | 0 | 281 |
| | α-B7 | 634 | 11 | 257 |
| | α-CD28 | 730 | 0 | 286 |
| −IL-2 | none | 601 | — | 79 |
| | CTLA-4 Ig | 164 | 72 | 36 |
| | β-cL6 | 444 | 26 | 100 |
| | β-B7 | 564 | 6 | 150 |
| | β-CD28 | 401 | 33 | 217 |

PBMC that were stimulated with soluble anti-CD3 (OKT3) and then cultured in the presence or absence of 30 U/ml exogenous IL-2 addition. MAb to L6 (cL6) or B7 (BB1) or CD28 (9.3) or the fusion protein CTLA-4 Ig were added at 10 $\mu$g/ml final concentration at time of anti-CD3 activation. The percent p24 inhibition was based on the mean of OKT3 induced HIV-1 from seven replicate wells.
S.I. = stimulation index (mean of stimulated cpm/mean of unstimulated) from incorporation of [$^3$H]Tdr.

Inhibition of HIV-1 production by mAb to adhesion molecules was not due to competition with anti-CD3 for Fc receptors. To assure that the viral inhibitory effects of mAb to adhesion molecules was not due to competition for monocyte Fc receptors with the activating α-CD3 mAb, F(ab')2 or Fab antibody to CD18/LFA-1 (60.3) and CD2 (9.6), respectively, was added to anti-CD3 activated PBMC.

Table 2 shows that more than 80% inhibition of HIV-1 production was effected by these non-Fc-binding mAb. These results show that the inhibition of HIV-1 production mediated by mAb to adhesion molecules is due to interruption of necessary cell-cell interactions necessary for efficient production of HIV-1. Inhibition of HIV-1 production was thus not due to competition for Fc receptor with the activating agent, α-CD3.

TABLE 2

Fc RECEPTOR BINDING IS NOT REQUIRED FOR ANTI-CD2 OR ANTI-LFA-1 INHIBITION OF HIV-1 PRODUCTION

| Anti-CD3 stimulation of PBMC | mAb | p24, ng/ml | % HIV Inhibition | S.I. |
|---|---|---|---|---|
| Z31 | none | 122 | — | 33 |
| | α-CD18 Fab'2 | 7 | 94 | 30 |
| | α-CD2 Fab | 22 | 82 | 38 |
| Z35 | none | 2328 | — | 57 |
| | α-CD18 Fab'2 | 337 | 85 | 54 |
| | α-CD2 Fab | 389 | 84 | 62 |

TABLE 2-continued

Fc RECEPTOR BINDING IS NOT REQUIRED FOR ANTI-CD2
OR ANTI-LFA-1 INHIBITION OF HIV-1 PRODUCTION

| Anti-CD3 stimulation of PBMC | mAb | p24, ng/ml | % HIV Inhibition | S.I. |
|---|---|---|---|---|

Fab α-CD2 (9.6) or Fab'2 α-CD18 (60.3) mAb (10 μg/ml) and IL-2 (30 U/ml) were added to PBMC at time of stimulation. PBMC were stimulated with soluble anti-CD3 (G19-4, 1 μg/ml) in the presence or absence of mAb to CD2 or CD18 for p24 measurement on day 11 post activation. Z31 and Z35 indicate PBMC, depleted of CD8+, B cells, and NK cells from asymptomatic HIV-1 seropositive patients.
S.I. = stimulation index (mean of stimulated cpm/mean of unstimulated) from incorporation of [$^3$H]Tdr.

MAb to adhesion molecules also inhibited HIV-1 production induced by staphylococcal enterotoxin (SAg). Unlike solube α-CD3, SAg requires monocyte major histocompatiblilty class II (MHC II) antigen presentation, but most SAg do not require antigen processing.

Table 3 shows that all of the adhesion molecules, except B7/CD28, that are important for HIV-1 production by anit-CD3 activation, are also important for HIV-1 production following activation by SAg. However, soluble CTLA-4 did not inhibit HIV-1 production induced by SAg even in the absence of exogenous IL-2. The lack of inhibition by CTLA-4 Ig in SAg stimulated PBMC was probably due to production of endogenous IL-2. Picomolar concentrations of SAg have been reported to induce vigorous T cell proliferation and release of large amounts of IL-2, γ-IFN, and TNF (C. D. Tsoukas et al., "Activation of Resting T Lymphocytes by Anti-CD3 (T3) Antibodies in the Absence of Monocytes," *J. Immunol.* 135:1719–1723 (1985); H. Fischer et al., "Production of TNF-α and TNF-β by Staphylococcal Enterotoxin A Activated Human T Cells," *J. Immunol.* 144:4663–4669 (1990)) and thus the potentional inhibitory effect of CTLA-4 Ig may have been overcome by endogenous IL-2 produced following SAg stimulation.

The chimeric humanized single-chanin antibody CD2 SFv-Ig of Example 1 was effective in blocking HIV-1 proliferation in CD4+ HIV-1 infected T cells. Concentration as low as 0.1 μg/ml of CD2 SFv-Ig inhibited HIV-1 production induced by anti-CD3 by more than 50% (FIG. 2). CD2 SFv-Ig did not inhibit CD4+ T cell proliferation as much as did mAb 35.1. In an experiment to test the effect of CD2 SFv-Ig on the SAg-induced HIV-1 production, CD2 SFv-Ig inhibited SAg-induced HIV-1 production from PBMC by 50–96% at 0.1–10 μg/ml without inhibition of T-cell proliferation, whether or not exogenous IL-2 was added.

MAb to CD6, CD5, CD14, CD11c (p180, 95) and CD44 did not inhibit HIV-1 production. Also, mAb to CD28, B7, CD11b (MAC-1) or CD7 did not have consistent inhibitory effects on HIV-1 production (FIG. 1, and Tables 1 and 3).

TABLE 3

ANTIBODIES TO ADHESION MOLECULES INHIBIT HIV-1
PRODUCTION INDUCED BY *STAPHYLOCOCCAL ENTEROTOXIN* ("SUPERANTIGEN")

| SAg Stimulation of PBMC | MAb or Protein added | p24, ng/ml | % HiV Inhibition | S.I. |
|---|---|---|---|---|
| Part a) | none | 83 | 79 | 79 |
|  | α-LFA-3 | 3 | 96 | 50 |
|  | α-CD2 | 7 | 92 | 40 |
|  | α-ICAM-1 | 2 | 98 | 54 |
|  | α-CD18 | 4 | 97 | 69 |
|  | α-MAC-1 (CD18/CD11b) | 77 | 7 | 48 |
| Part b) | none | 24 | — | 60 |
|  | CTLA-4 Ig | 91 | 0 | 60 |
|  | α-cL6 | 67 | 0 | 69 |

Part a) PBMC, depleted of CD8+, B cells, and NK cells, were activated with a cocktail of SAg (SEE, SEC2, and exfoliative toxin, 0.6 μg/ml each). MAb to LFA-3 (Ts 2/9), or CD2 (35.1), or ICAM-1 (84H10), or CD18 (60.3), or CD18/CD11b (60.1) were all added with 30 U/ml IL-2 at a final concentration of 10 μg/ml upon PBMC SAg activation.
Part b) In a separate experiment, PBMC were activated with the same SAg cocktail as in part (a) without addition of exogenous IL-2. CTLA-4 Ig protein or human cL6 mAb, control, was added (10 μg/ml) to PBMC at time of activation and supernatant was assayed after 7 days.
S.I. = stimulation index (mean of stimulated cpm/mean of unstimulated) from incorporation of [$^3$H]Tdr.

These results suggest that therapy of HIV-1 infected patients can be targeted at T cell-monocyte interactions that we have shown to be important for HIV-1 production. The chimeric humanized anti-CD2 antibody, CD2 SRv-Ig, can be useful for this therapy.

Example 3

Competition of CD2 SFv-Ig with Chimeric Murine Anti-CD2 Monoclonal Antibody for Binding to CD2 Antigen In order to ensure that the CD2 SFv-Ig chimeric humanized antibody bound to the same epitope as the murine monoclonal antibody 35.1 from which it was derived, competition experiments were carried out in which both mAb 35.1 and CD2SFv-Ig competed with labeled mAb 35.1 for binding to CD2 on Jurkat T cells as determined by FACS.

Jurkat T cells ($10^6$) were incubated with 10-fold serial dilutions of unlabelled anti-CD2 (35.1), CD2 SFv-Ig, or CD5-Ig control, for 90 minutes on ice in staining medium (RPMI 1640 medium+5% fetal calf serum+0.1% sodium azide) in 0.2 ml total volume, prior to the addition of fluorescein isothiocyanate (FITC) labelled 35.1 mAb (anti-CD2) at 1:3000 dilution in staining medium. Cells were washed and analyzed by FACS.

Figure 3:
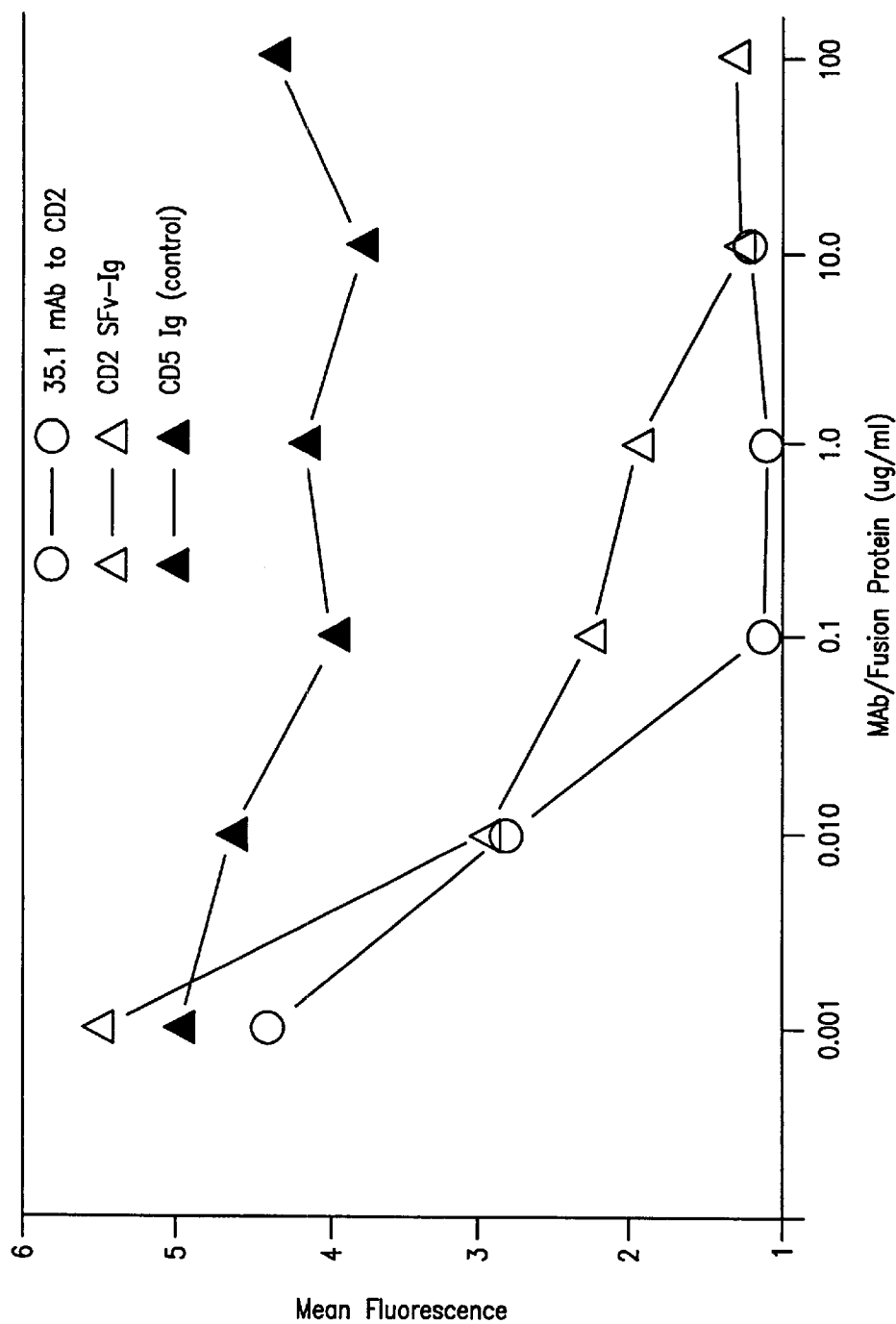
FIG. 3 is a graph showing, by fluorescence-activated cell sorting, that chimeric single-chain recombinant antibody CD2 SFv-Ig competes effectively with murine anti-CD2, monoclonal antibody 35.1 for binding to CD2 antigen on Jurkat T cells.

The results are shown in FIG. 3. CD2 SFv-Ig competed effectively with MAb 35.1 for binding to CD2 antigen, indicating that it bound to the same epitope.

ADVANTAGES OF THE INVENTION

The present invention provides a chimeric humanized single-chain recombinant antibody to CD2 antigen, CD2 SFv-Ig, that can inhibit proliferation of HIV-1 virus in infected T cells. The monoclonal antibody evokes a minimal immune response and is better tolerated than native murine monoclonal anitibodies. The present invention also provides methods of using antibodies, including chimeric humanized antibodies according to the present invention, to inhibit proliferation of HIV-1 as a method of treating or palliating AIDS, either in vivo or ex vivo. This method preserves T-cell function while suppressing HIV-1 replication. It is particularly useful in treatment of opportunistic infection that frequently accompany AIDS and can be used together with therapies for such opportunistic infections.

Although the present invention has been described in considerable detail with regard to certain preferred versions thereof, other versions are possible. Therefore, the spirit and scope of the appended claims should not be limited to the descriptions of the preferred versions contained herein.

SEQUENCE LISTING

<160> NUMBER OF SEQ ID NOS: 4

<210> SEQ ID NO 1
<211> LENGTH: 16
<212> TYPE: PRT
<213> ORGANISM: Unknown
<220> FEATURE:
<223> OTHER INFORMATION: Description of Organism: Synthesized

<400> SEQUENCE: 1

Glu Ser Gly Ser Val Ser Ser Glu Glu Leu A la Phe Arg Ser Leu Asp
 1               5                  10                  15

<210> SEQ ID NO 2
<211> LENGTH: 84
<212> TYPE: DNA
<213> ORGANISM: Unknown
<220> FEATURE:
<223> OTHER INFORMATION: Description of Organism: Synthesized

<400> SEQUENCE: 2
aagcaagagc attttcctga tcaggagccc aaatcttctg acaaaactca c acatcccca      60 ccgtccccag cacctgaact cctg                                              84

<210> SEQ ID NO 3
<211> LENGTH: 41
<212> TYPE: DNA
<213> ORGANISM: Unknown
<220> FEATURE:
<223> OTHER INFORMATION: Description of Organism: Synthesized

<400> SEQUENCE: 3
cttcgaccag tctagaagca tcctcgtgcg accgcgagag c                           41

<210> SEQ ID NO 4
<211> LENGTH: 15
<212> TYPE: PRT
<213> ORGANISM: Unknown
<220> FEATURE:
<223> OTHER INFORMATION: Description of Organism: Synthesized

<400> SEQUENCE: 4

Glu Pro Lys Ser Ser Asp Lys Thr His Thr S er Pro Pro Ser Pro
 1               5                  10                  15

We claim:

1. A method for inhibiting the production of HIV-1 in HIV-1 infected PBMC consistently essentially of the steps of:

(a) selecting and isolating PBMC infected with HIV-1; and (b) contacting said infected PBMC with at least one antibody or ligand in a quantity sufficient to inhibit the production of HIV-1 in said T cells, wherein said antibody or ligand is selected from the group consisting of:

(i) an antibody selected from the group consisting of:
 (1) an antibody having specific binding affinity for CD2 antigen selected from the group consisting of single-chain recombinant antibody CD2 SFv-IG produced by expression of the construct cloned in recombinant *Escherichia coli* culture NO. ATCC 69277, an antibody having complementarity-determining regions identical with those of CD2 SFv-Ig, and an antibody competing with CD2 SFv-Ig for binding to CD2 antigen at least about 80% as effectively on a molar basis as CD2 SFv-Ig;

(2) another antibody to CD2 that is a monoclonal antibody;
(3) a monoclonal antibody to CD18;
(4) a monoclonal antibody to counter-receptor LFA-3; and
(5) a monoclonal antibody to counter-receptor ICAM-1; and
(ii) a LFA-3 ligand comprising the extracellular domain of LFA-3 in soluble form.

2. The method of claim 1, wherein said antibody is specific for CD2 and blocks the binding of CD2 antigen with its counter receptor LFA-3.

3. The method of claim 2, wherein said antibody is an antibody having specific binding affinity for CD2 antigen, said antibody being selected from the group consisting of:

(i) single-chain recombinant antibody CD2 SFv-Ig;
(ii) an antibody competing with CD2 SFv-Ig for binding to the CD2 antigen at least about 80% as effectively on a molar basis as CD2 SFv-Ig and having at least one sequence segment of at least five amino acids of human orgin;
(iii) an antibody competing wiht SFv-Ig for binding to the CD2 antigen at least about 80% as effectively on a molar basis as CD2 SFv-Ig and having at least one sequence segment of at least five amino acids of human origin.

4. The method of claim 3, wherein said antibody is single-chain recombinant antibody CD2 SFv-Ig.

\* \* \* \* \*

UNITED STATES PATENT AND TRADEMARK OFFICE
CERTIFICATE OF CORRECTION

PATENT NO. : 6,384,198 B1
DATED : May 7, 2002
INVENTOR(S) : Diegel et al.

It is certified that error appears in the above-identified patent and that said Letters Patent is hereby corrected as shown below:

<u>Title page,</u>
Item [73], Assignee: change "Sqibb" to -- Squibb --.

<u>Column 25,</u>
Line 62, change "consistenly" to -- consisting --.

<u>Column 26,</u>
Line 1, change "T cells" to -- PBMC --.

Signed and Sealed this

Twenty-second Day of October, 2002

Attest:

JAMES E. ROGAN
Attesting Officer     Director of the United States Patent and Trademark Office